US007485121B2

(12) United States Patent
Noon et al.

(10) Patent No.: US 7,485,121 B2
(45) Date of Patent: Feb. 3, 2009

(54) MIDFACE DISTRACTOR

(75) Inventors: John M. Noon, Paoli, PA (US); Paul Christopher Ciccone, Lincoln University, PA (US)

(73) Assignee: Synthes (USA), West Chester, PA (US)

( * ) Notice: Subject to any disclaimer, the term of this patent is extended or adjusted under 35 U.S.C. 154(b) by 434 days.

(21) Appl. No.: 10/839,551

(22) Filed: May 4, 2004

(65) Prior Publication Data
US 2005/0251136 A1  Nov. 10, 2005

(51) Int. Cl.
*A61B 17/60* (2006.01)
(52) U.S. Cl. .......................................... 606/90
(58) Field of Classification Search ............. 606/54–57, 606/59, 71, 86, 90, 96, 98, 105; 600/227, 600/228, 231, 232, 235; 602/32, 36
See application file for complete search history.

(56) References Cited

U.S. PATENT DOCUMENTS

| | | | |
|---|---|---|---|
| 2,360,738 A | | 10/1944 | Stevenson |
| 3,072,118 A | * | 1/1963 | Standerwick et al. ......... 602/17 |
| 3,391,693 A | | 7/1968 | Georgiade et al. |
| 3,927,664 A | | 12/1975 | Georgiade et al. |
| 4,096,857 A | | 6/1978 | Cramer et al. |
| 4,612,930 A | | 9/1986 | Bremer |
| 5,147,358 A | | 9/1992 | Remmler |
| 5,364,396 A | | 11/1994 | Robinson et al. |
| 5,524,859 A | * | 6/1996 | Squires et al. ............... 248/551 |
| 5,540,687 A | | 7/1996 | Fairley et al. |
| 5,672,177 A | | 9/1997 | Seldin |

(Continued)

FOREIGN PATENT DOCUMENTS

DE  4219156  12/1993

(Continued)

OTHER PUBLICATIONS

KLS Martin L.P., Product Information: Rigid External Distraction RED II system.

(Continued)

*Primary Examiner*—Eduardo C Robert
*Assistant Examiner*—Michael J Araj
(74) *Attorney, Agent, or Firm*—Woodcock Washburn LLP

(57) ABSTRACT

An external midface distractor is disclosed for attachment to the bones of a patient's cranium and midface region for performing an osteogenesis procedure to gradually lengthen a portion of the craniofacial skeleton. The midface distractor generally includes an external halo assembly for engaging the patient's cranium, a central adjustment assembly, a vertical central rod, at least one horizontal cross piece assembly including at least one distraction screw, and at least one bone engaging portion which is mounted to the targeted facial bone to be distracted. The midface distractor may also include various individual adjustment mechanisms that provide surgeons greater and more precise control over the distraction vector than is available with current devices. That is, the midface distractor may provide surgeons with additional anterior-posterior and medial-lateral adjustments, thus permitting surgeons to more precisely and accurately control the direction of distraction. The midface distractor may also permit surgeons to easily and accurately alter the direction of distraction after the distraction procedure has commenced thereby providing surgeons the ability to readjust the ultimate vector of distraction anytime during the procedure, as necessary.

100 Claims, 18 Drawing Sheets

U.S. PATENT DOCUMENTS

| | | | |
|---|---|---|---|
| 5,681,313 | A | 10/1997 | Diez |
| 5,769,850 | A | 6/1998 | Chin |
| 5,807,382 | A | 9/1998 | Chin |
| 5,810,812 | A | 9/1998 | Chin |
| 5,846,245 | A | 12/1998 | McCarthy et al. |
| 5,855,580 | A | 1/1999 | Kreidler et al. |
| 5,885,283 | A | 3/1999 | Gittleman |
| 5,885,289 | A | 3/1999 | Muller |
| 5,885,290 | A | 3/1999 | Guerrero et al. |
| 5,895,387 | A | 4/1999 | Guerrero et al. |
| 5,902,304 | A | 5/1999 | Walker et al. |
| 5,968,043 | A * | 10/1999 | Ross et al. .................... 606/56 |
| 5,976,142 | A | 11/1999 | Chin |
| 5,993,448 | A | 11/1999 | Remmler |
| 6,113,599 | A | 9/2000 | Landsberger |
| 6,171,313 | B1 | 1/2001 | Razdolsky et al. |
| 6,176,859 | B1 | 1/2001 | Muller |
| 6,187,004 | B1 | 2/2001 | Fearon |
| 6,277,124 | B1 | 8/2001 | Haag |
| 6,293,947 | B1 | 9/2001 | Buchbinder |
| 6,322,566 | B1 | 11/2001 | Minoretti et al. |
| 6,423,069 | B1 | 7/2002 | Sellers |
| 6,471,706 | B1 | 10/2002 | Schumacher et al. |
| 6,520,961 | B1 * | 2/2003 | Marsh ......................... 606/54 |
| 6,547,796 | B1 | 4/2003 | Chin |
| 6,565,576 | B1 | 5/2003 | Stauch et al. |
| 7,011,642 | B2 * | 3/2006 | Greene et al. ................. 602/36 |
| 2002/0035368 | A1 | 3/2002 | Schumacher |
| 2002/0040225 | A1 | 4/2002 | Sellers et al. |
| 2002/0072747 | A1 | 6/2002 | Cohen et al. |
| 2002/0116002 | A1 | 8/2002 | Sellers |
| 2002/0156485 | A1 | 10/2002 | Sellers et al. |
| 2002/0161374 | A1 | 10/2002 | Cohen et al. |
| 2005/0043730 | A1 * | 2/2005 | Janowski et al. .............. 606/56 |

FOREIGN PATENT DOCUMENTS

| | | |
|---|---|---|
| WO | WO 9809577 | 3/1998 |

OTHER PUBLICATIONS

W. Lorenz Surgical, Product Information: Blue Device: multi-vector distraction.

Three-dimensional midface distraction by Harry C. Schwartz and John Beumer III.

Irby head frame design (1955).

* cited by examiner

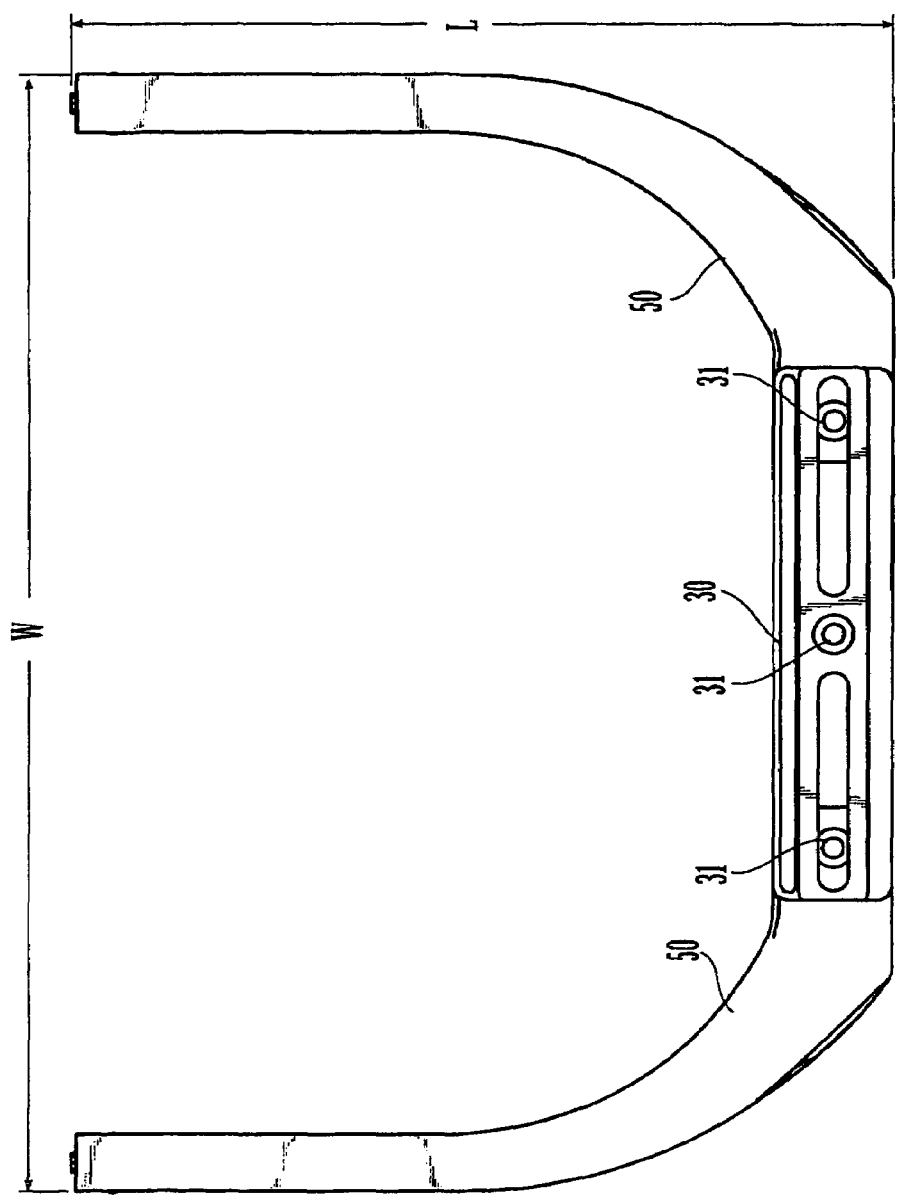

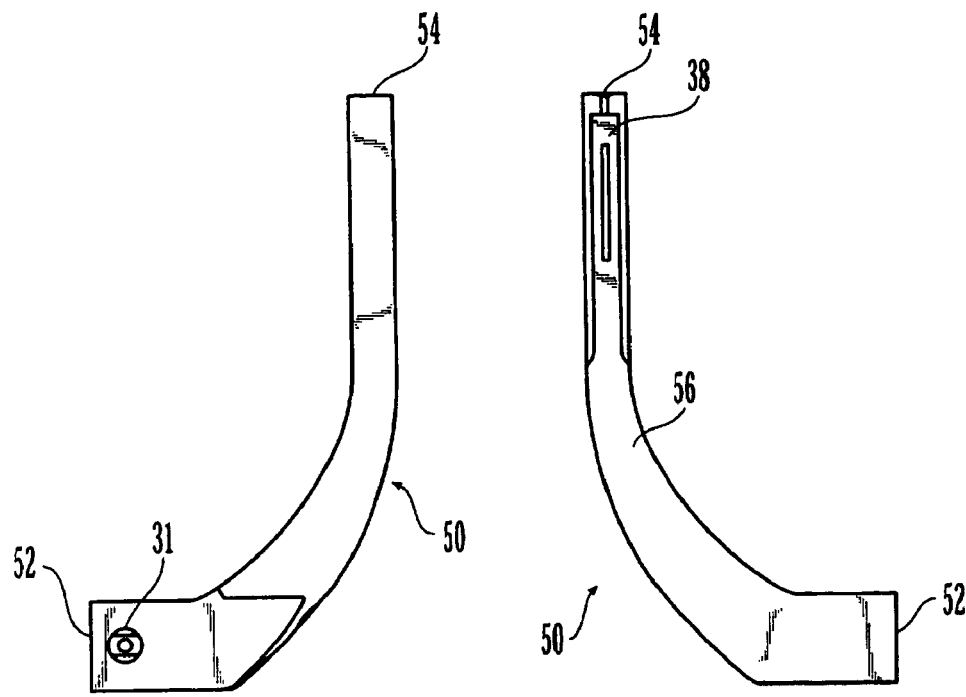
*Fig. 4A*  *Fig. 4B*
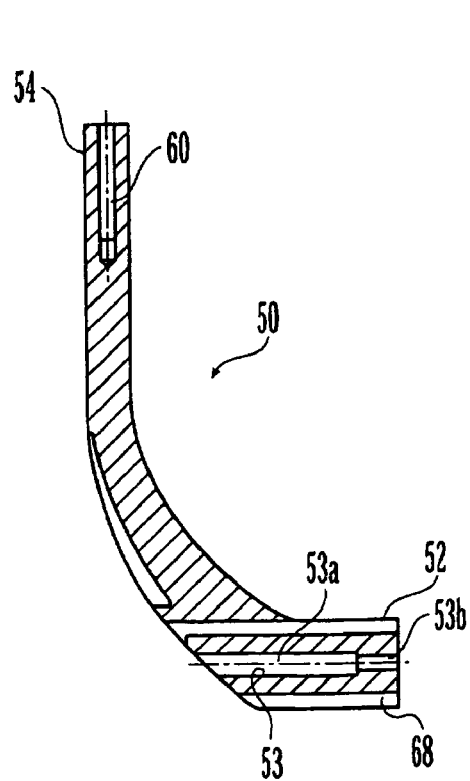 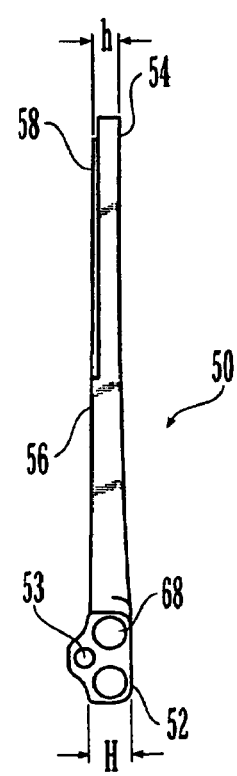
*Fig. 4C*  *Fig. 4D*

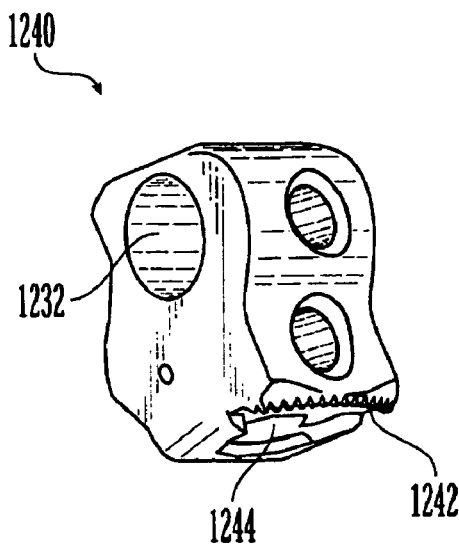
Fig. 15A
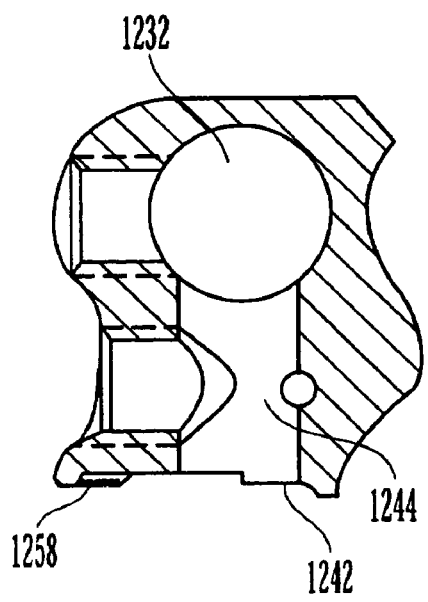 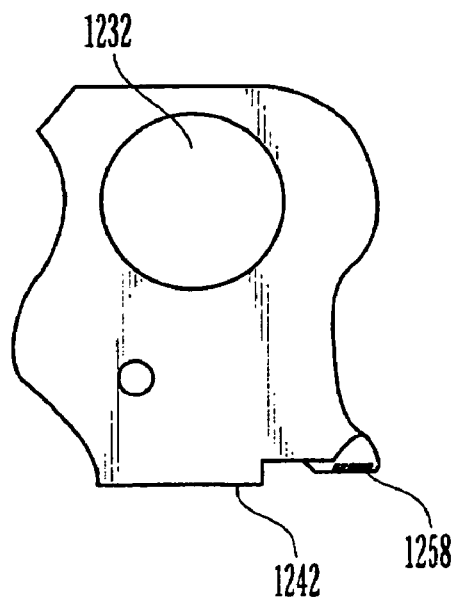
Fig. 15B            Fig. 15C

MIDFACE DISTRACTOR

FIELD OF INVENTION

The present invention relates to a midface distractor. More particularly, the present invention relates to an external apparatus for the gradual lengthening (i.e., distraction) of a portion or portions of the craniofacial skeleton. The midface distractor may incorporate adjustment mechanisms that provide surgeons with greater and more precise control over the distraction vector than current devices. That is, the midface distractor may provide surgeons with anterior-posterior and medial-lateral adjustment thus providing surgeons with virtually unlimited control over the ultimate distraction vector. Furthermore, the midface distractor may also permit surgeons to alter the distraction vector both before and after the distraction procedure has commenced.

BACKGROUND OF THE INVENTION

Generally speaking, distraction procedures or distraction osteogenesis has become an important treatment vehicle for patients with craniofacial abnormalities. Today when a child or an adult suffers from a craniofacial abnormality, such as an overbite jaw or cleft palate, they may undergo a distraction osteogenesis procedure in which the surgeon cuts through certain bones of the face (often called LeFort I, II, III or Monobloc cuts) and installs a bone lengthening device (i.e., an external midface distractor) that attaches to the patient's bones on either side of the cuts. The external distractor is thereafter used to gradually separate (i.e. distract) the bone segments in order to achieve the desired new facial configuration.

It is an object of the present invention to provide a midface distractor that incorporates various individual adjustment mechanisms to allow a surgeon greater and more precise control over the ultimate distraction vector than current devices. It is a further object of the present invention to provide a midface distractor that permits a surgeon to easily and accurately alter the direction of distraction after the distraction procedure has commenced.

SUMMARY OF THE INVENTION

The present invention relates to an external midface distractor for attachment to the bones of a patient's cranium and midface region for performing an osteogenesis procedure to gradually lengthen a portion or portions of the craniofacial skeleton. The midface distractor generally includes an external halo assembly, for engaging the patient's cranium, a central adjustment assembly, a vertical central rod, at least one horizontal cross piece assembly including at least one distraction screw, and at least one bone engaging portion, which is mounted to the targeted facial bone to be distracted. The midface distractor may also include various individual adjustment mechanisms which enable the distractor to be sized and configured to fit virtually anyone regardless of their own individual characteristics. The midface distractor may also include various individual adjustment mechanisms that provide surgeons greater and more precise control over the distraction vector than currently available devices. That is, the midface distractor may provide surgeons with additional anterior-posterior and medial-lateral adjustments, thus permitting surgeons to more precisely and accurately control the direction of distraction. Furthermore, the midface distractor may permit surgeons to easily and accurately alter the direction of distraction after the distraction procedure has commenced thereby providing a surgeon the ability to readjust the ultimate vector of distraction anytime during the procedure as necessary.

The halo assembly of the present invention may be any halo assembly known in the art. Alternatively, the halo assembly of the present invention may be a U-shaped member that includes two mounting plates, each having a plurality of cranial fixation bores, two side members, and a central connection hub for interconnecting the two side members and for connecting the halo assembly to the central adjustment assembly. The halo assembly may incorporate adjustment mechanisms which permit the halo to be sized to fit an individual patient's head. That is, the halo assembly may incorporate a medial-lateral adjustment mechanism for adjusting the overall width "W" of the halo assembly, and an anterior-posterior mechanism within each side piece for adjusting the overall length "L" of the halo assembly.

The central adjustment assembly of the present invention connects the halo assembly to the vertical central rod, thus supporting the vertical central rod, and its associated horizontal rods, clamps and distraction screws, in front of the patient's face. The central adjustment assembly may be any mechanism known in the art for connecting the halo assembly with a vertical rod, including but not limited to a non-adjustable single piece. Alternatively, the central adjustment assembly may incorporate a variety of adjustment mechanisms for permitting multiple adjustments of the vertical central rod. That is, the central adjustment assembly may permit rotation of the vertical central rod about the superior-inferior and medial-lateral axes, and also may permit vertical and medial-lateral directional adjustment of the vertical central rod.

The vertical central rod of the present invention is a longitudinal rod that interconnects the central adjustment assembly and the horizontal cross-piece assemblies. The vertical central rod permits the horizontal cross-piece assemblies and the central adjustment assembly to be located virtually anywhere along its length, thus providing maximum freedom in determining placement of the horizontal cross-piece assemblies, distraction screws and footplates. The vertical central rod preferably includes a slot extending longitudinally along its outer surface, the slot being sized and configured to mate with and engage set screws in the central adjustment assembly and horizontal cross-piece assemblies, respectively. The mating of the slot and set screws prevents rotation of the vertical central rod with respect to the central adjustment assembly and horizontal cross-piece assemblies.

The horizontal cross-piece assemblies of the present invention connect the vertical central rod to the distraction screws, which connect to bone engaging portions via footplate assemblies. The midface distractor may include any number of horizontal cross-piece assemblies. The number of horizontal cross-piece assemblies may generally be dependent upon the type of procedure, i.e., osteotomy, being performed. For example, the midface distractor may include two horizontal cross piece assemblies, one to engage the maxillary bones and the other to engage the zygomatic bones. The horizontal cross-piece assemblies may provide mechanisms for providing lateral adjustment, transverse rotation, and superior-inferior directional control over the position of the distraction screws. Generally speaking, the horizontal cross-piece assemblies include a central clamp, a horizontal rod, and at least one distractor clamp. The central clamp connects the vertical central rod with the horizontal rod. The horizontal rod may be generally oriented along an axis perpendicular to the longitudinal axis of the vertical central rod, and connects the central clamp and the distractor clamp(s), which may be located on either side of the central clamp. The distractor clamp(s) generally include a pair of bores, one for receiving the horizontal rod and one for receiving a distraction screw. The distractor clamp(s) may be located virtually anywhere along the length of the horizontal rod, thus permitting the surgeon to adjust the lateral placement of the distraction screws and footplates attached thereto. Moreover, the distractor clamp(s) may rotate about the horizontal rod, thus permitting surgeons to vary the angle of the distraction screws with respect to the horizontal rod, thereby providing additional control over the angle and direction of distraction, particularly in the superior-inferior direction. The distraction clamps may also incorporate a swivel feature to allow adjustment of the distraction screw about an axis parallel to the vertical rod. Thus providing surgeons with an additional adjustment option in fixing the location of the distraction screws, and in turn, over the ultimate direction of distraction.

The distraction screws of the present invention may generally be oriented perpendicular to both the vertical central rod and the horizontal rod of the horizontal cross-piece assemblies, however, the swivel-type distractor clamp may allow adjustment of this orientation. The distraction screws generally have a distal end that points inward toward the patient's face, and a proximal end which engages the distractor clamp. The distal end of each distraction screw may include a hole drilled therethrough for receiving a wire, which is used to connect the distraction screw with a corresponding footplate assembly. It should be noted however, that using a wire is not critical and that the distraction screws may directly engage the bone-engaging portions instead.

The footplate assemblies of the present invention connect the distraction screws to the bone segments to be distracted. Generally speaking, the midface distractor may incorporate any number of footplate assemblies. The midface distractor may incorporate maxillary and zygomatic footplate assemblies which connect maxilla and zygoma bone segments with respective distraction screws. The maxillary footplate assembly generally includes a bone engaging portion for directly engaging the maxilla, a distractor-engaging portion, and a rod portion for connecting the bone-engaging portion to the distractor-engaging portion. The zygomatic footplate assembly generally includes a bone engaging portion for engaging a patient's zygoma, and a wire attachment screw having a first end and a second end. The first end of the wire attachment screw is sized and configured to threadedly engage and extend through a bore in the bone engaging portion so that the first end of the screw may also threadedly engage the patient's zygomatic bone. The second end of the wire attachment screw generally includes an enlarged head with a hole drilled therethrough for engaging a respective distraction screw via a wire. It should be noted that the maxillary and zygomatic footplate assemblies and their arrangements as described are preferred embodiments only and surgeons may if they so desire use only maxillary footplate assemblies, or only zygoma footplate assemblies. Furthermore, surgeons may attach the zygoma footplate assemblies to the patient's maxilla, and attach the maxillary footplate assemblies to the patient's zygoma. Finally, the distraction screws may connect to the bone-engaging portions directly or via a wire, thus simplifying the maxillary and zygoma footplate assemblies. Alternatively, the maxillary bone-engaging portion may be eliminated and the apparatus may be attached to a patient's teeth using a rigid intra-oral splint.

In use, the midface distractor is attached to a patient's cranium. That is, a surgeon fits the halo assembly to a patient's head by adjusting the lateral and longitudinal adjustment mechanisms of the halo assembly and attaching the bone engaging portions to the targeted bone segments. The surgeon then selects the number of horizontal cross-piece assemblies desired. The horizontal cross-piece assemblies may then be attached to the vertical central rod, which is attached to the central adjustment assembly, which may already be connected to the halo assembly. The vertical central rod is then adjusted and aligned to avoid interference with the patient's eyesight. Next, the surgeon sets the angle of the distraction screws based upon his/her determination as to the appropriate initial vector of distraction. The angle of the distraction screws may be set by adjusting the location and angle of: the vertical central rod, the central adjustment assembly, and the horizontal cross-piece assemblies including the horizontal rod and distractor clamps. The surgeon then may attach the distraction screws to the bone-engaging portions. Thereafter, the midface distractor is fixed into place by tightening set screws included throughout for each purpose. Lastly, the surgeon confirms the advancement of the desired bone segments. Once properly installed, the bone segments may be subjected to gradual incremental distraction by rotation of the distraction screws. The distraction screws may be periodically (e.g. daily) rotated to incrementally distract the bone segment (usually by about 1 mm), until the desired distraction is achieved. The ultimate rate, rhythm, direction, and amount of distraction is left to the determination of the surgeon.

BRIEF DESCRIPTION OF THE DRAWINGS

FIG. 3 is a top view of the halo assembly depicted in FIG. 2.

FIG. 4a is a top view of the side member of the halo assembly depicted in FIGS. 2 and 3.

FIG. 4b is a bottom view of the side member depicted in FIG. 4a.

FIG. 4c is a sectional view of the side member depicted in FIG. 4b.

FIG. 4d is a side view of the side member depicted in FIGS. 4a-4c.

FIG. 5b is a top view of the mounting plate depicted in FIG. 5a.

FIG. 6b is a front sectional view of the connection hub depicted in FIG. 6a.

FIG. 14b is a sectional view of the distractor clamps shown in FIG. 14a.

FIG. 15a is a perspective view of the top portion of the distractor clamp of the horizontal cross-piece assembly depicted in FIG. 12.

FIG. 15b is a sectional view of the top portion of the distractor clamp depicted in FIG. 15a.

FIG. 15c is a side view of the top portion of the distractor clamp depicted in FIG. 15a.

FIG. 16b is a side view of the bottom portion of the distractor clamp depicted in FIG. 16a.

DESCRIPTION OF THE PREFERRED EMBODIMENTS

Figure 1:
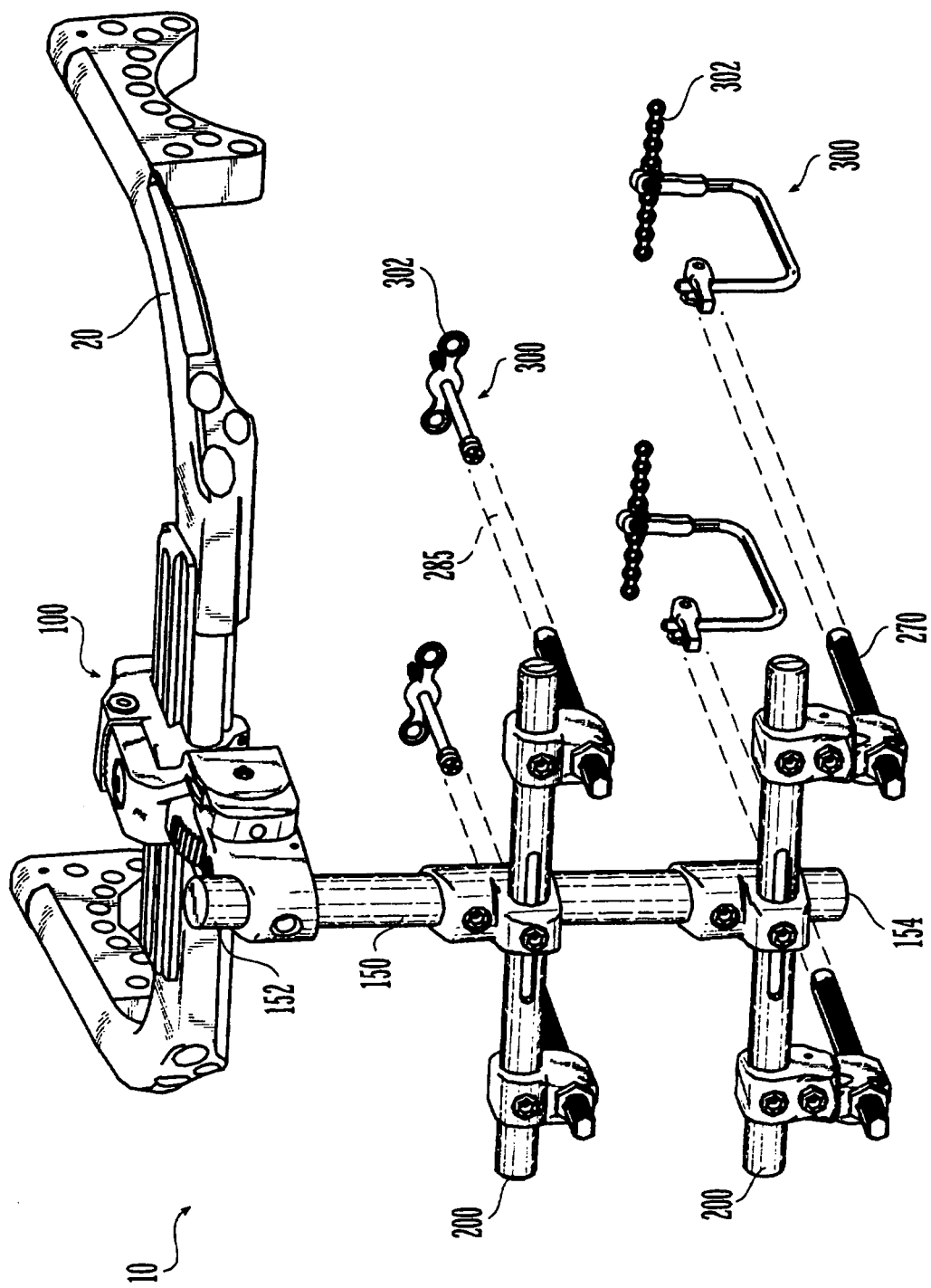
FIG. 1 is a perspective view of the midface distractor according to one embodiment of the present invention.

For the purpose of promoting an understanding of the principles of the present invention, reference will now be made to an exemplary, non-limiting embodiment illustrated in FIG. 1. The midface distractor 10 is directed to an external apparatus for attachment to the bones of a patient's cranium and midface region for performing an osteogenesis procedure to gradually lengthen a portion or portions of the craniofacial skeleton. As shown, the midface distractor 10 includes: an external halo assembly 20 for engaging the patient's cranium, a central adjustment assembly 100 including a vertical central rod 150 attached thereto, at least one horizontal cross piece assembly 200 including at least one distraction screw 270, and at least one footplate assembly 300 which is mounted to the targeted craniofacial bone to be distracted. The midface distractor 10 may also include various individual adjustment mechanisms that enable the midface distractor to conform to most patient's regardless of their individual physical characteristics.

The midface distractor 10 may also include various individual adjustment mechanisms to provide surgeons greater and more precise control over the distraction vector than currently available devices. That is, the midface distractor 10 may provide surgeons with additional anterior-posterior and medial-lateral adjustments, thus permitting surgeons to more precisely and accurately control the direction of distraction. Furthermore, the midface distractor 10 may also permit surgeons to easily and accurately alter the direction of distraction after the distraction procedure has commenced thereby providing surgeons the ability to readjust the ultimate vector of distraction anytime during the procedure, if necessary.

Halo Assembly

The halo assembly may be a structural frame that attaches to a patient's head to provide a rigid support structure for the distraction elements. Halo assemblies are known in the art, and any known halo assembly may be used in combination with the present invention. For example, the halo assembly may be a single unitary piece that encircles and attaches to a patient's head without any adjustment mechanisms.

Figure 2:
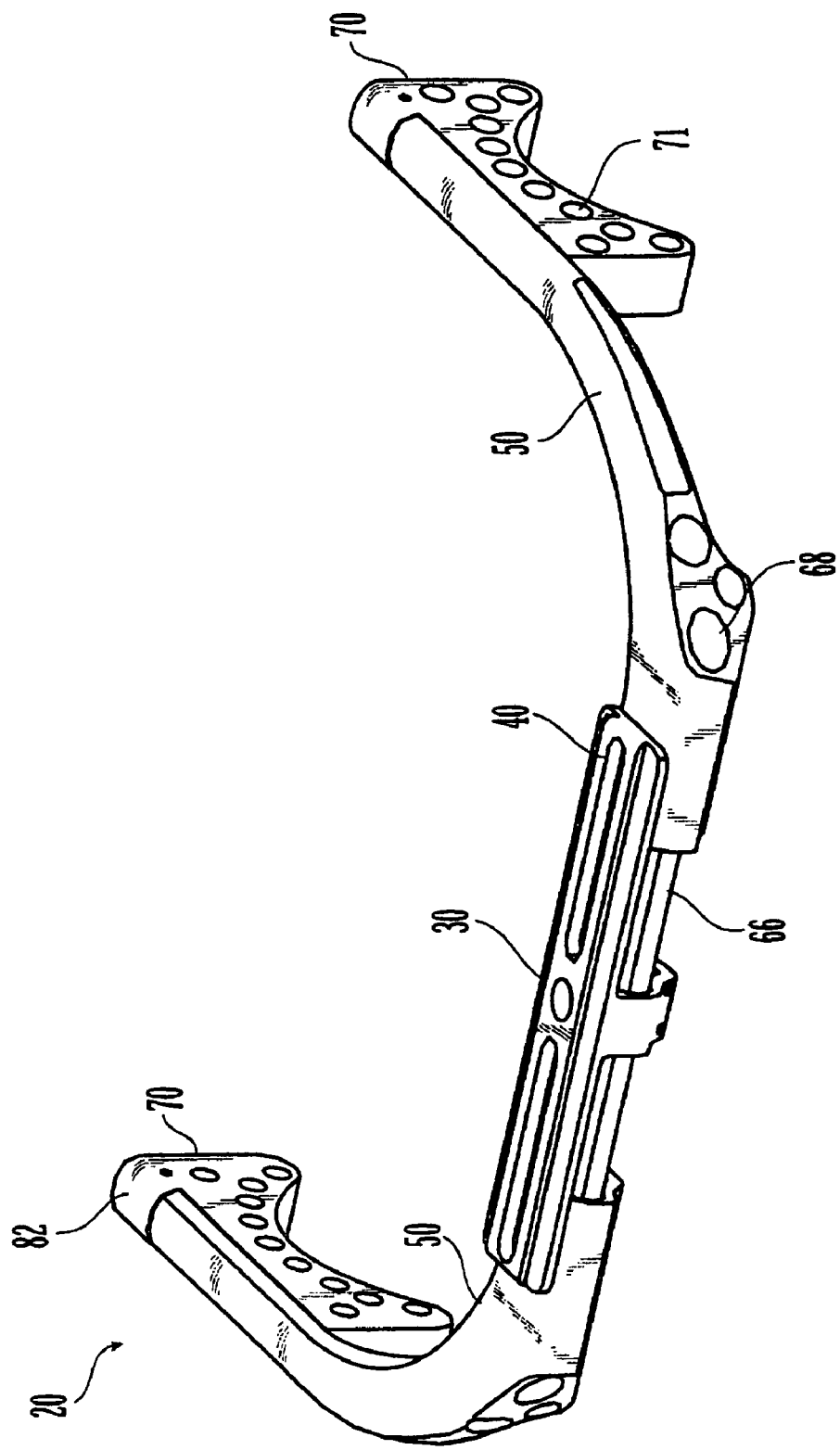
FIG. 2 is a perspective view of the halo assembly according to one embodiment of the present invention.

Alternatively, as shown in FIGS. 2 and 3, the halo assembly 20 may be a U-shaped member that includes two mounting plates 70, each having a plurality of cranial fixation bores 71, two side members 50, and a central connection hub 30 for interconnecting the two side members 50 and for connecting the halo assembly 20 to the central adjustment assembly 100. Furthermore, the halo assembly 20 may also include adjustment mechanisms that permit the halo to be sized to an individual patient's head. That is, the halo assembly 20 may incorporate, either alone or in combination, a medial-lateral adjustment mechanism for adjusting the overall width "W" of the halo assembly, and an anterior-posterior mechanism within each side member 50 for adjusting the overall length "L" of the halo assembly 20.

The side members 50 of the halo assembly 20, when viewed from above, may each generally be an "L" shaped member, with each side member 50 designed to wrap around a respective side of the patient's head. The side members 50 may be designed to provide the halo assembly 20 with a streamlined look while simultaneously providing the lightest possible structure. As shown in FIGS. 4a-4d, each side member 50 may include a front portion 52 and a rear portion 54, and the front portion 52 may be radiused in order to provide the patient with a better fitting, better looking, more comfortable halo assembly 20. The front portion 52 may also be configured to engage one side of the connection hub 30 (see FIGS. 6a through 6c), while the rear portion 54 may be configured to engage a mounting plate 70.

Figure 5A:
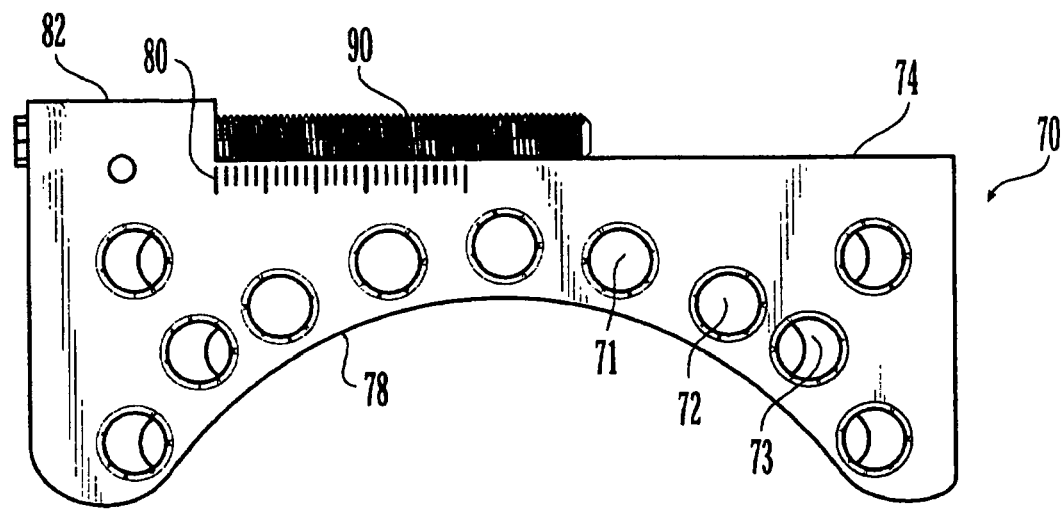
FIG. 5a is a side view of the mounting plate of the halo assembly depicted in FIGS. 2 and 3.
Figure 5B:
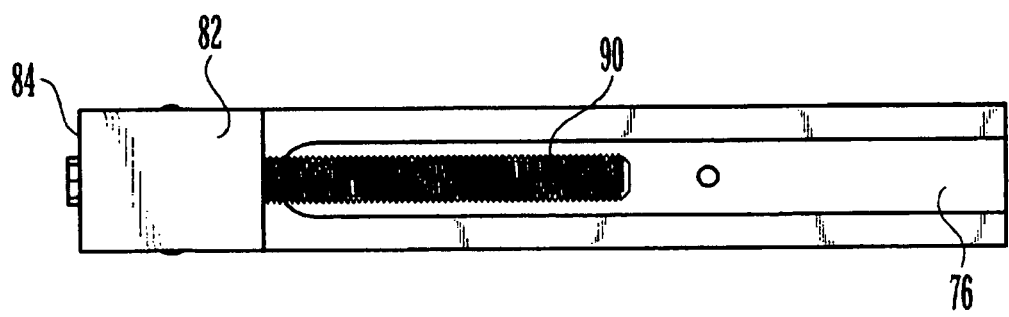

As best shown in FIGS. 5a and 5b, the mounting plates 70 may be designed to fit over a patient's ear for fixing the halo assembly 20 to a patient's skull by any method known in the art. Thus, although the mounting plates 70 may take any shape, configuration or contour, each mounting plate 70 may generally be a rectangular plate having an arcuate cut-out formed along its bottom surface 78, which provides an improved contoured fit around the patient's ear.

The mounting plates 70 may include a plurality of bores 71 extending through the mounting plate 70 to the other so that skull fixation means (not shown) may be inserted in discrete locations above the patient's ears in the temporal and/or parietal bones of the skull to fix the plate to the skull. The plurality of bores 71 may be of any size, shape or dimension appropriate for receiving the skull fixation means. The bores 71 may also be threaded so that the halo assembly 20 may be fixed to the patient's head by externally threaded skull fixation pins (not shown). The skull fixation pins may be inserted through the bores 71 of the mounting plates 70 positioned above the patient's ears. Use of threaded bores 71 in combination with threaded skull fixation pins permits the fixation pins to be partially threaded into the mounting plates 70 prior to placing the halo assembly 20 around the patient's cranium thereby simplifying the installation process. In addition, the fixation pins may have finely pointed ends configured to pierce the skin, thus eliminating the need for making pre-incisions in the patient's scalp. Alternatively, the skull fixation means may include self-drilling mounting pins (not shown) which actively engage the skull through a bone thread. Furthermore, the midface distractor 10 may be provided with positional pins (not shown) which are sized and configured to temporarily position the location of the halo assembly 20 with respect to the patient's scalp. Once properly positioned, the positional pins can be removed and replaced with permanent skull fixation means.

The bores 71 may be oriented such that their axes may be perpendicular to the plane of the mounting plates 70. Alternatively, the bores 71 may be angled relative to the plane of the mounting plates 70; the degree of such an angle being that appropriate for the particular patient and/or procedure, for example, the bores may have a 15 degree angle with respect to the plane of the mounting plates. The mounting plates 70 may also incorporate a combination of straight 72 and angled 73 bores, with the straight bores 72 being located generally in the middle of the plate 70 and the angled bores 73 being located along the outer edges of the plate 70. However, any combination and arrangement of straight 72 and angled 73 bores is permissible.

The mounting plates 70 may be connected to the side members 50 by any method known in the art including but not limited to welding, gluing, etc. Alternatively, the mounting plates 70 may be formed integrally with the side members 50 of the halo assembly 20 or they may be omitted entirely with the side members 50 instead containing a plurality of bores 71 for receiving the skull fixation means. The mounting plates 70 may also be adjustably connected to the side members 50 thereby permitting the overall length "L" of the halo assembly 20 to be adjusted. In one embodiment, the bottom surface 56 of the rear portion 54 of the side member 50 may contain a projection 58 for engaging a slot 76 in the top surface 74 of the mounting plate 70 thus allowing the mounting plates 70 to slide in the anterior-posterior direction along the side member 50. The projection 58 may be, for example, a dovetail for engaging a corresponding groove in the top surface 74 of the mounting plate 70. Furthermore, the rear portion 54 of each side member 50 may also include an internally threaded bore 60 for engaging a first end of an adjustment screw 90. The top surface 74 of the mounting plate 70 may contain an upwardly extending portion 82 having a bore 84 for rotatably receiving the second end of the adjustment screw 90. The adjustment screw 90 may be axially retained within the mounting plate bore 84, so that rotation of the adjustment screw 90 causes the side member 50 to move with respect to both the adjustment screw 90 and the mounting plate 70. Thus, rotating the adjustment screw 90 may cause the side member 50 to move within the slot 76 along the mounting plate 70. Rotating the adjustment screw 90 in a first direction may cause the mounting plate 70 to pull the side member 50 closer to it, thereby decreasing the overall length "L" of the halo assembly 20. Rotating the adjustment screw 90 in a second direction may cause the mounting plates 70 and the side members 50 to move further apart thereby increasing the overall length "L" of the halo assembly 20. As shown, the adjustment screw 90 may allow the length "L" of the halo assembly 20 to be increased by up to about 25 millimeters (mm) beyond its unextended length. Preferably, as shown, in FIG. 5a, the mounting plates 70 may include calibrations, for example, markings 80 to help the surgeon calculate the amount of adjustment.

Connection Hub

As previously noted, each side member 50 may have a front portion 52 that, when installed, is positioned adjacent the middle of the patient's forehead. The connection hub 30 may interconnect the front portion 52 of each side member 50 together, while also providing a mechanism for the halo assembly 20 to be connected to the remainder of the distraction device via a central adjustment assembly 100 (to be described in more detail later). As generally shown in FIG. 4d, the height "h" of the side member 50 may increase from the rear portion 54 to the front portion 52, thus facilitating connection of the side members 50 to the connection hub 30 while minimizing weight and streamlining the halo's overall appearance.

Figure 6A:
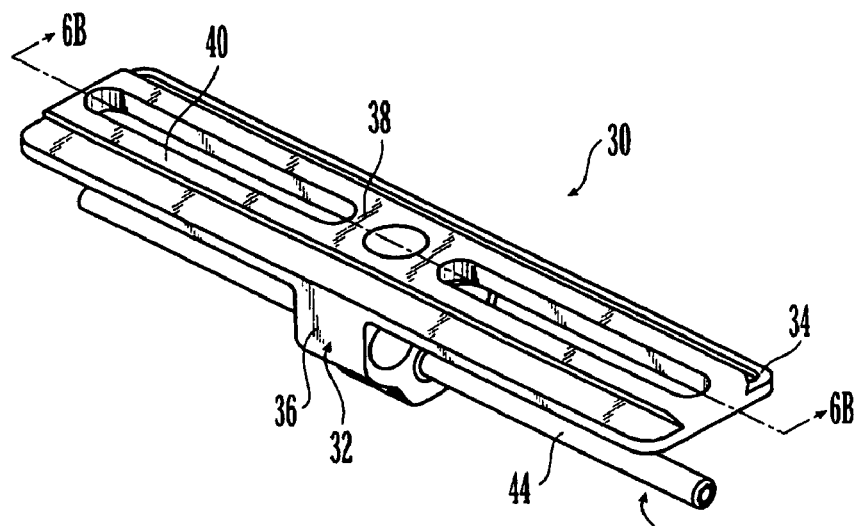
FIG. 6a is a perspective view of the connection hub of the halo assembly depicted in FIGS. 2 and 3.
Figure 6B:
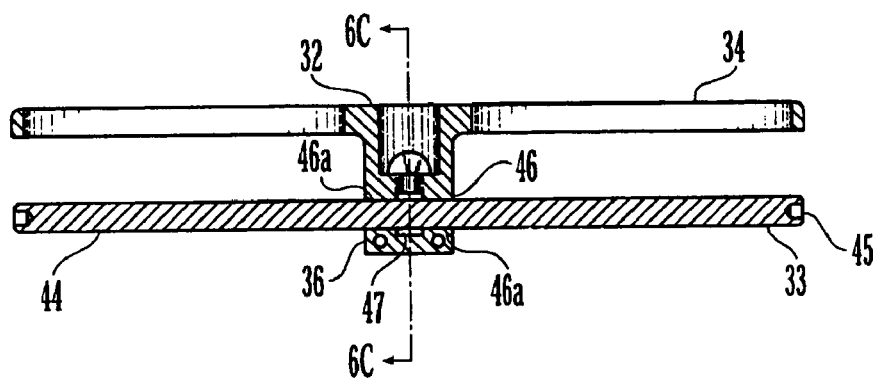
Figure 6C:
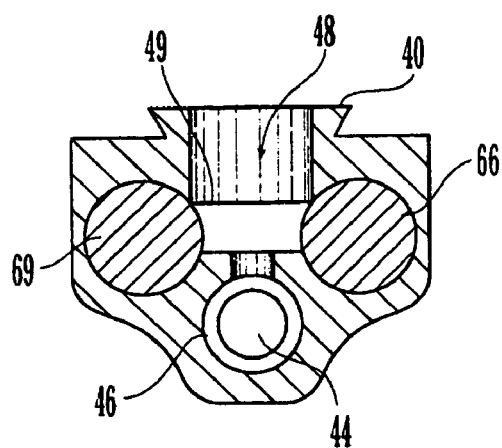
FIG. 6c is a side view of the connection hub shown in FIGS. 6a and 6b.

As shown in FIGS. 6a-6c, the connection hub 30 generally includes a center piece 32 and a lateral adjustment mechanism 33 for adjusting the overall width "W" of the halo assembly 20. The center piece 32 may be any shape known in the art including, but not limited to, a square, rectangle, etc. In the illustrated embodiment, the center piece 32 has a T-shaped profile with a top portion 34 and a bottom portion 36. The top portion 34 may be configured to engage the central adjustment assembly 100, while the bottom portion 36 may be configured to receive the lateral adjustment mechanism 33.

The bottom portion 36 of the center piece 32 may contain a mechanism for engaging the lateral adjustment mechanism 33. The lateral adjustment mechanism 33 may be any mechanism known in the art appropriate for adjusting the position of interconnected members including, but not limited to, a rack and pinion, a standard screw, a worm gear type mechanism, etc. In the illustrated embodiment, the bottom portion 36 of the center piece 32 contains a horizontal bore 46 for receiving a frame adjustment screw 44, i.e., a double threaded screw containing screws of opposite hand on either end that mate with corresponding bores 53 formed in the front portion 52 of the side members 50. The horizontal bore 46 formed in the connection hub 30 may also be provided with a bearing member 46a sized and configured to surround and mate with the adjustment screw 44. The bearing member 46a may be press fit and pinned within the horizontal bore 46 after the adjustment screw 44 has been placed therein to thereby fix the axial position of the adjustment screw 44 with respect to the connection hub 30. As shown, one bearing member 46a may be placed on either side of a groove 47 formed on the adjustment screw 44.

Moreover, as best shown in FIG. 4c, the bore 53 formed in the side member 50 may include a larger diameter, non-threaded portion 53a and a smaller diameter, threaded portion 53b. The threaded portion 53b may be sized and configured to threadedly engage the adjustment screw 44, while the non-threaded portion 53a may be sized and configured to receive a tool, for example, a screwdriver, a ratchet, etc., for engaging a tool engagement mechanism 45 located on either end of the adjustment screw 44 to allow the user to rotate the adjustment screw 44 in the desired direction. When assembled to the side members 50, the ends of the frame adjustment screw 44 may be accessible through the bore 53 which extends through each side member 50.

Thereafter, rotation of the frame adjustment screw 44 in a first direction may cause the side members 50 of the halo assembly 20 to be drawn toward the connection hub 30 thereby reducing the overall width "W" of the halo assembly 20. Similarly, rotating the frame adjustment screw 44 in a second direction may cause the side members 50 to move away from the connection hub 30, thereby increasing the halo's overall width "W". The frame adjustment screw 44 may permit from about 0 mm to about 40 mm of adjustment on each side of the connection hub 30.

To prevent twisting of the side members 50 with respect to each other and to the connection hub 30, and to allow smooth lateral adjustment of the halo 20, the lateral adjustment mechanism 33 may also incorporate at least one, and preferably two, reinforcing rods 66 (shown in FIG. 2), located parallel to, and on either side of, the adjustment screw 44. However, any number and configuration of reinforcing rods 66 may be used. Each rod 66 may be designed and configured to fit within corresponding recesses 68, 69 formed in the side members 50 and connection hub 30, respectively, so that the rods 66 may be generally slidable within the recesses 68, 69.

Thus, when the adjustment screw 44 is rotated, the side members 50 may slide along the rods 66, and be guided thereon for smooth movement.

The connection hub 30 and the side members 50 may also include a locking mechanism 31 for fixing the overall width "w" of the halo assembly 20 once it has been determined. Although any number of locking mechanisms 31 may be used, as best shown in FIG. 3, preferably the distractor 10 includes three locking mechanisms 31, one on each of the side members 50 and one on the connection hub 30. The locking mechanism 31 may be any mechanism known in the art appropriate for fixing the relative position of moveable members including, but not limited to, a standard set screw. However, as best shown in FIG. 6c, the locking mechanism 31 may include a screw 48 and a rod lock 49. The screw 48 and rod lock 49 may be sized and configured to extend through a bore in the hub 30 so that the rod lock 49 contacts the outer circumference of the reinforcing rods 66. The screw 48 may be sized and configured to extend through the rod lock 49 and into a groove 47 formed in the adjustment screw 44. Thereafter, rotation of the screw 48 may cause the rod lock 49 to bear down on the reinforcing rods 66 thus fixing the position of the reinforcing rods 66 with respect to the connection hub 30. Although the locking mechanism 31 has been described in conjunction with the connection hub 30, as previously stated, each side member 50 may also include a locking mechanism 31 identical to the one described above.

The top portion 34 of the connection hub 30 may include an attachment mechanism for connecting the connection hub 30 to the central adjustment assembly 100. The attachment mechanism may be any means known in the art including, but not limited to, screwing, welding, etc. In the illustrated embodiment, the superior surface 38 of the top portion 34 of the center piece 32 may have a projection 40 orientated generally parallel to the axis of the frame adjustment screw 44 (i.e., the medial-lateral axis when the device is mounted on the patient) for engaging a corresponding slot 112 located in the central adjustment assembly 100. The projection 40 may be a dovetail for engaging a corresponding groove located in the central adjustment assembly 100, thus permitting the surgeon to slide the central adjustment assembly 100 along the medial-lateral axis of the connection hub 30. Thus, a surgeon may use this attachment mechanism to adjust the lateral position of the vertical central rod 150 (to be discussed later) to a desired position in front of the patient's face to minimize any interference with the patient's eyesight. The top portion 34 of the connection hub 30 is sized and configured so that it may receive and engage two central adjustment assemblies 100 simultaneously so that, if a surgeon desires, he/she may install two central adjustment mechanisms 100 and two corresponding vertical central rods 150. Thus, providing surgeons with an additional adjustment mechanism to enable greater and more precise control over the distraction vector. It also enables surgeons to space the vertical central rods 150 out toward the periphery of a patient's eyesight away from his/her central vision, thus minimizing the amount of interference with the patient's eyesight.

The connection hub 30 may further include a groove (not shown) for receiving a set screw 114 on the central adjustment mechanism 100 so that when the central adjustment mechanism 100 and corresponding vertical central rod 150 are properly positioned, rotation of the set screw 114 fixes the lateral position of the central adjustment mechanism 100 with respect to the connection hub 30. Preferably, the set screw 114 and groove are sized and configured so that the set screw 114 may be loosened to enable the central adjustment assembly 100 to move with respect to the connection hub 30. However, even in the loosened condition, the set screw 114 and groove are sized and configured so that the set screw 114 can not be removed from the groove thus, preventing the connection hub 30 and central adjustment mechanism 100 from separating.

The side members 50, connection hub 30, and reinforcing rods 66 may be manufactured from any material known in the art including, but not limited to, titanium, aluminum, stainless steel, polymers, carbon fiber, etc. Preferably, the connection hub 30 is anodized titanium, which provides lubrication for facilitating slidable movement between the hub 30 and the central adjustment mechanism 100.

Central Adjustment Assembly

Figure 7:
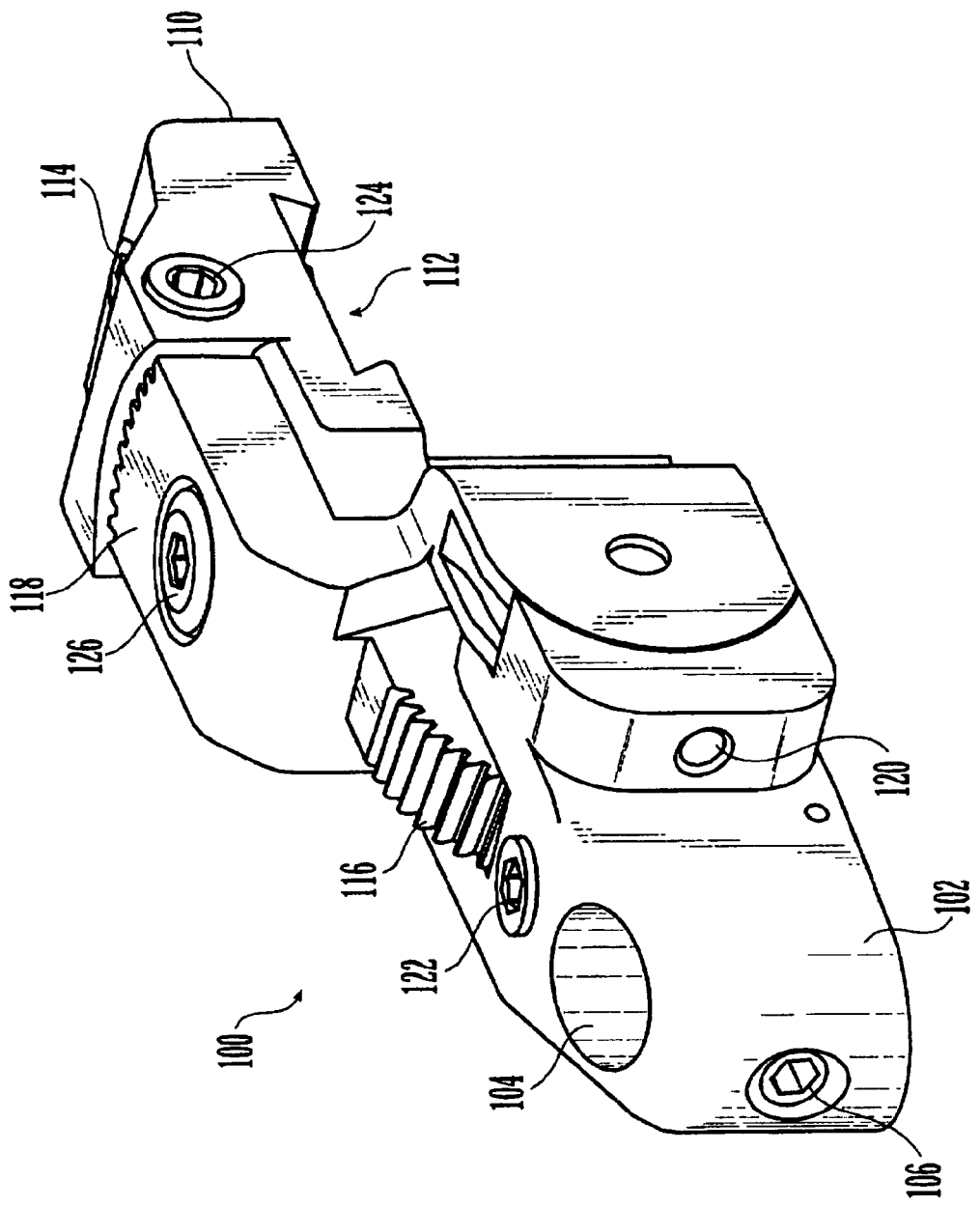
FIG. 7 is a perspective view of the central adjustment assembly depicted in FIG. 1.
Figure 10:
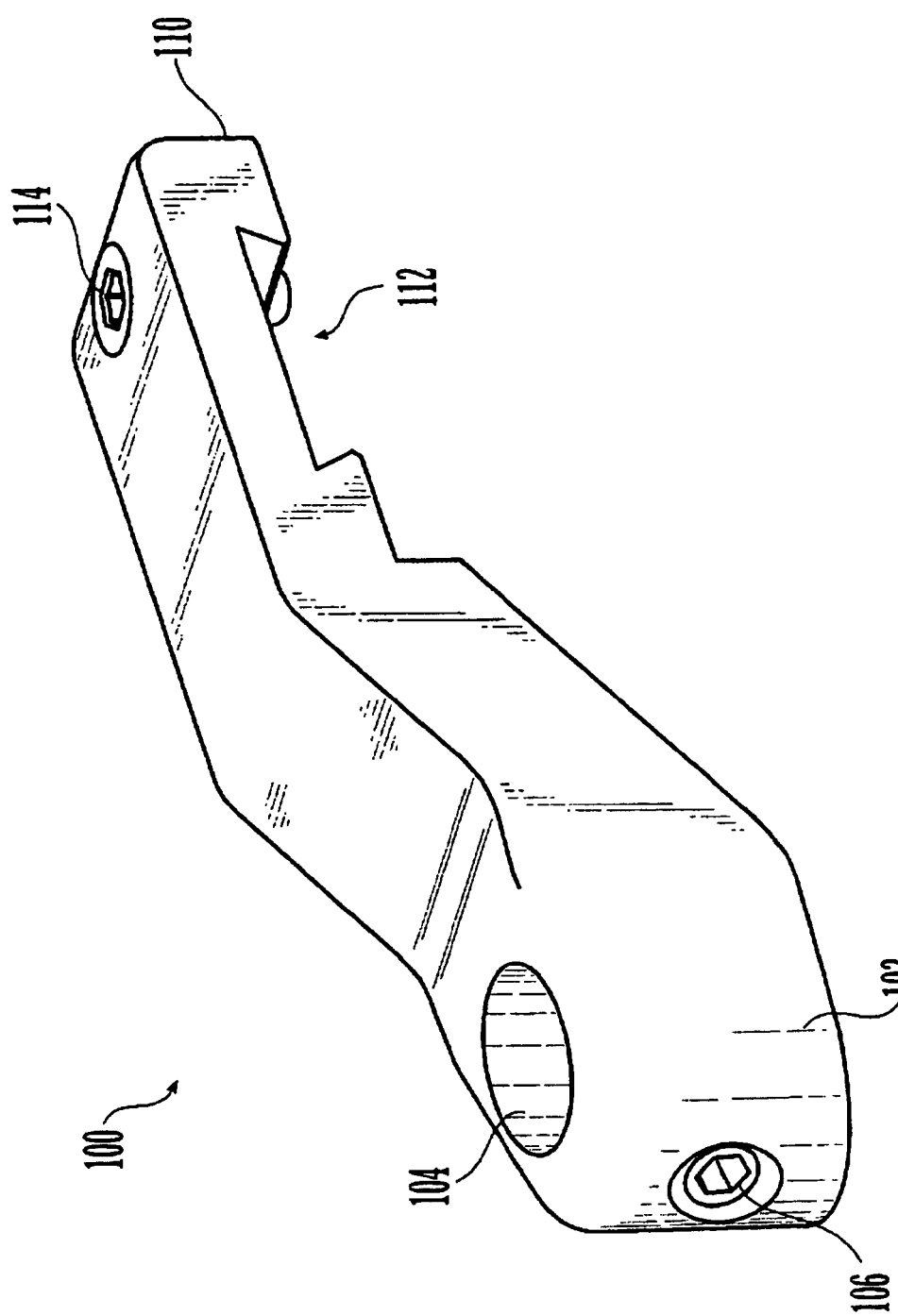
FIG. 10 is an alternate embodiment of a central adjustment assembly according to the present invention.

As best shown in FIG. 1, the central adjustment assembly 100 connects the halo assembly 20 to the vertical central rod 150, thus supporting the vertical central rod 150, and its associated horizontal rods, clamps and distraction screws, at a desired location in front of the patient's face. Any mechanism for connecting the halo assembly 20 with a vertical central rod 150 may be used including, but not limited to, for example, a single unitary piece as shown in FIG. 10. Preferably, however, as best shown in FIG. 7, the central adjustment assembly 100 may incorporate a variety of individual adjustment mechanisms for permitting adjustment of the vertical central rod 150 with respect to the halo assembly 20. That is, the central adjustment assembly 100 may permit, either alone or in combination, rotation of the vertical central rod 150 about the superior-inferior axis, about the medial-lateral axis, and may also permit medial-lateral and vertical adjustment of the vertical central rod 150.

As shown in FIG. 7, the central adjustment assembly 100 may include a front portion 102 and a rear portion 110. The rear portion 110 of the central adjustment assembly 100 mates with the attachment means of the connection hub 30. That is, as previously described, the rear portion 110 of the central adjustment assembly 100 may incorporate a slot 112 for engaging the corresponding projection 40 located on the superior surface 38 of the top portion 34 of the connection hub 30. The projection may be a dovetail which engages a corresponding groove located on the central adjustment assembly 100. This permits the surgeon to slide the central adjustment assembly 100 along the medial-lateral axis of the connection hub 30. Thus, a surgeon may adjust the lateral position of the vertical rod 150 to its desired position in front of the patient's face to minimize interference with the patient's eyesight. As previously stated, the rear portion 110 may also incorporate a set screw 114 to fix the lateral position of the central adjustment assembly 100 with respect to the connection hub 30 once the medial-lateral and vertical position of the vertical rod 150 have been selected by the surgeon.

The front portion 102 of the central adjustment assembly 100 may extend anteriorly outward from the halo assembly 20, and mates via a bore 104 to an upper portion of the vertical central rod 150 which, at a lower portion, connects to the horizontal cross-piece assemblies 200 (as will be described in more detail later). The bore 104 may have an axis that is generally orientated substantially perpendicular to the top surface of the central adjustment assembly 100. The bore 104 may have a non-circular or keyed cross-section, for mating with a non-circular or keyed vertical central rod. Preferably, however, the rod 150 has a slot (not shown) extending longitudinally along its outer surface, the slot being sized and configured to mate with and engage a set screw 106 in the central adjustment assembly 100. The mating of the set screw 106 with the slot prevents rotation of the vertical central rod 150 with respect to the center adjustment assembly 100.

Moreover, rotation of the set screw 106 may also secure the axial position of the vertical central rod 150 with respect to the central adjustment assembly 150 once the rod 150 has been properly positioned by the surgeon.

As previously stated, the central adjustment assembly 100 may also incorporate, either alone or in combination, a variety of adjustment mechanisms for permitting additional adjustment of the vertical central rod 150 with respect to the halo assembly 20. That is, the central adjustment assembly 100 may be configured to permit angular adjustment of the vertical central rod 150 about a superior-inferior axis and a medial-lateral axis (thus allowing a wide variety of angular adjustment of the horizontal cross-piece assemblies 200, which may be attached thereto). This angular adjustment may be provided by any mechanism known in the art, including but not limited to a rack and pinion, spherical joint, a ratchet and pawl type assembly, a cam and follower type assembly, etc. Alternatively, as shown in FIG. 10, the central adjustment assembly 100 may be provided as a non-adjustable single piece which connects the halo assembly 20 to the vertical central rod 150. Preferably, however, as shown in FIG. 7, the central adjustment assembly 100 incorporates a variety of individual adjustment mechanisms for permitting adjustment of the vertical central rod 150 with respect to the halo assembly 20. As shown, the central adjustment assembly 100 may include at least one worm-gear mechanism located between the front 102 and rear 110 portions of the central adjustment assembly 100. As shown, the center adjustment mechanism 100 may include two worm gear mechanisms 116,118, although any number of worm gear mechanisms may be used. The worm gear mechanisms 116, 118 may have worm screws 122, 124, which may be located on the top or side surfaces of the central adjustment assembly 100. Utilization of worm gear mechanisms 116, 118 allows the surgeon to rotate the worm gears and vertical rod 150 a discrete and precise amount with each turn of the worm screws 122, 124 thereby permitting precise control over adjustments to the distraction vector. The pitch of the worm screw and worm gear threads may be selected to provide the desired amount of movement of the gear per degree of rotation of the screw 122, 124; that being a matter of design choice.

Figure 8:
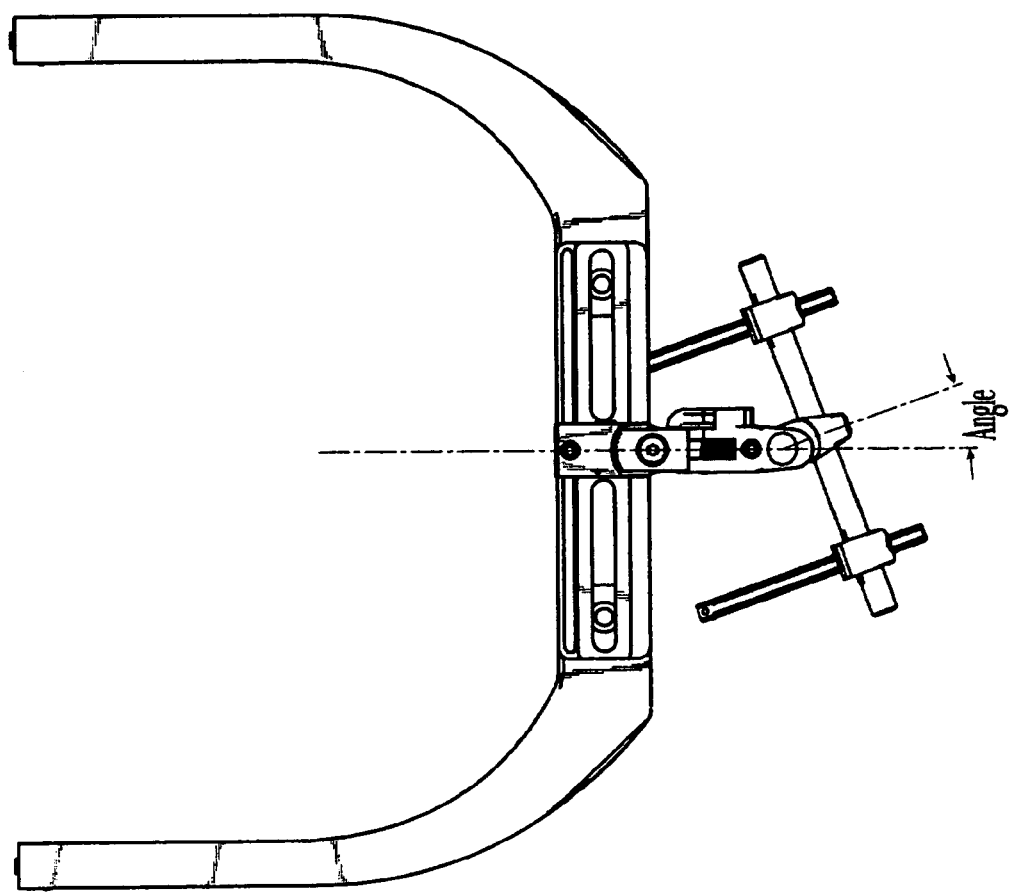
FIG. 8 is a top view of the central adjustment assembly and halo assembly depicted in FIGS. 1, 2, 3, and 7.
Figure 9:
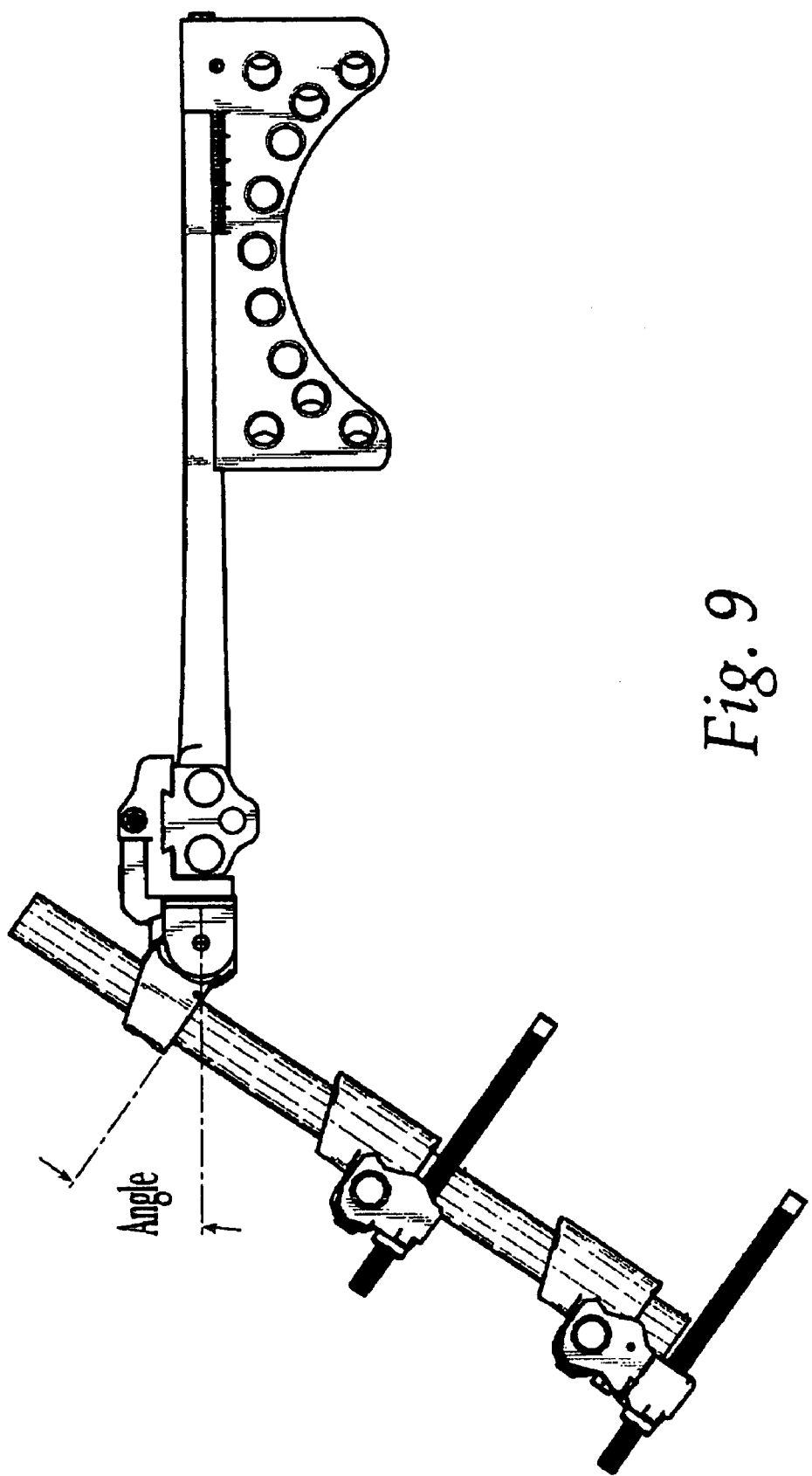
FIG. 9 is a side view of the central adjustment assembly and halo assembly depicted in FIGS. 1, 2, 3, and 7.

As shown, the first worm gear 116 permits superior-inferior rotation of the vertical central rod 150 (i.e., rotation about a medial-lateral axis) while the second worm gear 118 permits medial-lateral rotation of the vertical central rod 150 (i.e., rotation about a superior-inferior axis. That is, an axis perpendicular to a plane passing horizontally through the wearer's body). The worm gear mechanisms 116, 118 of the central adjustment assembly 100 may permit approximately +/−30 degrees of medial-lateral rotation and +45 to −30 degrees of superior-inferior rotation, as shown in FIGS. 8 and 9, although other rotational ranges are possible.

Each worm gear mechanism 116, 118 may also include a set screw 120, 126. Once tightened, the set screws 120, 126 prevent any further movement of the central adjustment assembly 100.

Vertical Central Rod

As shown in FIG. 1, the vertical central rod 150 may be a rod having a first end 152 and a second end 154. The first end 152 slidably engages the bore 104 of the central adjustment assembly 100, while the second end 154 slidably engages a central clamp 202 on the horizontal cross-piece assemblies 200 (to be discussed in more detail later). The vertical central rod 150 permits the horizontal cross-piece assemblies 200 and the central adjustment assembly 100 to be located virtually anywhere along its length, thus providing maximum freedom in determining placement of the horizontal cross-piece assemblies 200, distraction screws 270 and bone-engaging portions 302. Once the vertical central rod 150 has been properly positioned, set screws 106, 206 in the central adjustment assembly 100 and central clamp 202, respectively, may be tightened thereby preventing further movement of the vertical central rod 150.

As previously stated, the vertical central rod 150 preferably has a longitudinal slot extending along its outer surface, the slot being sized and configured to mate with a set screw 106 in the central adjustment assembly 100 and to mate with a set screw 206 in the central clamp 202, to be explained in more detail later, thereby preventing rotation of the vertical central rod 150 with respect to the central adjustment assembly 100 and with respect to the central clamp 202.

The vertical central rod 150 may be manufactured from any material known in the art including, but not limited to, aluminum, titanium, nitinol, polymers, carbon fiber material, etc.

Horizontal Cross-Piece Assemblies

The horizontal cross-piece assemblies 200 connect the vertical central rod 150 to the distraction screws 270, which themselves connect to the footplate assemblies 300. As shown in FIG. 1, the midface distractor 10 may include two horizontal cross piece assemblies 200, one to provide distraction of the maxillary bones and the other to provide distraction of the zygomatic bones. However, any number of horizontal cross-piece assemblies 200 may be utilized. For example, in a Lefort I surgical procedure typically only one horizontal cross-piece assembly 200 may be required, for example, to distract the maxilla.

The horizontal cross-piece assemblies 200 may provide mechanisms for allowing additional adjustment of the distraction vector. The horizontal cross-piece assemblies 200 may include mechanisms for providing lateral adjustment, transverse rotation, and superior-inferior directional control over the position of the distraction screws 270.

Figure 11:
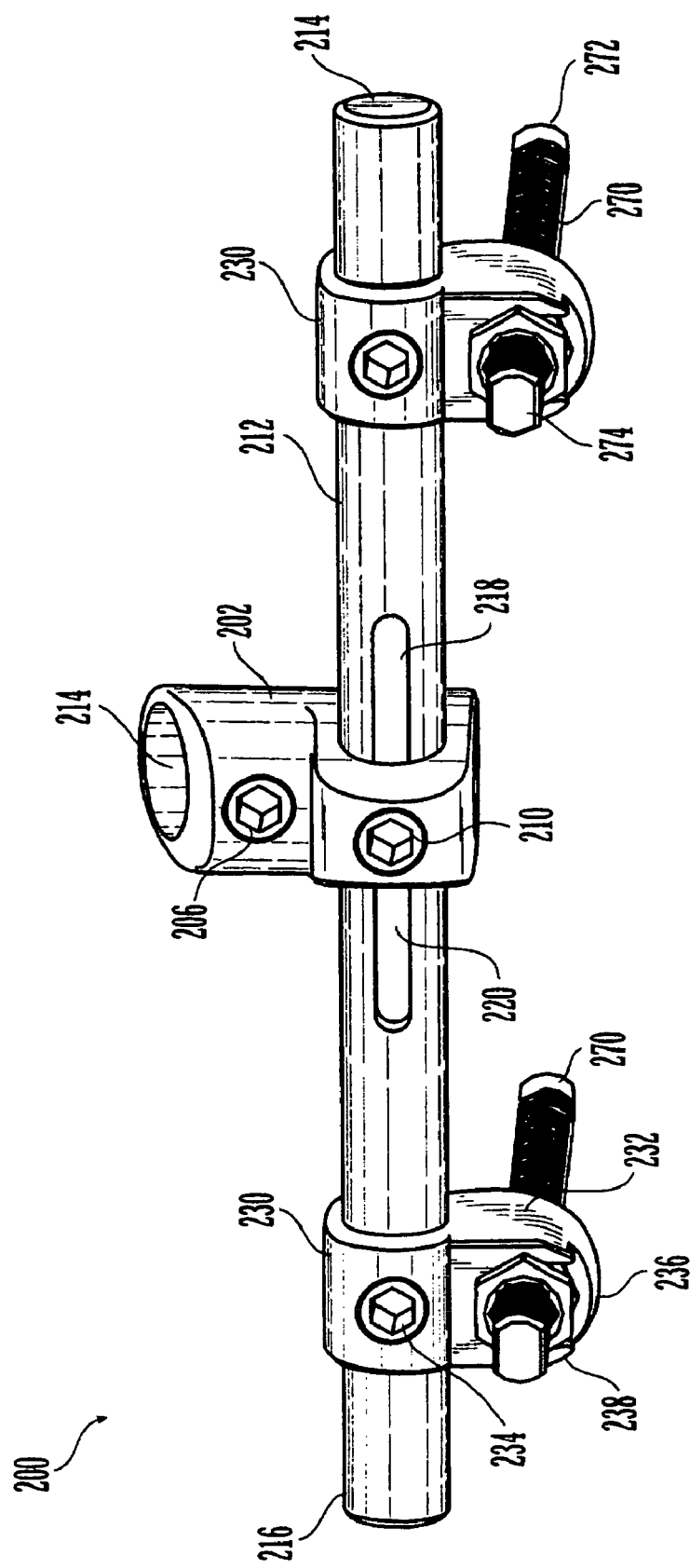
FIG. 11 is a perspective view of one embodiment of the horizontal cross-piece assembly.
Figure 12:
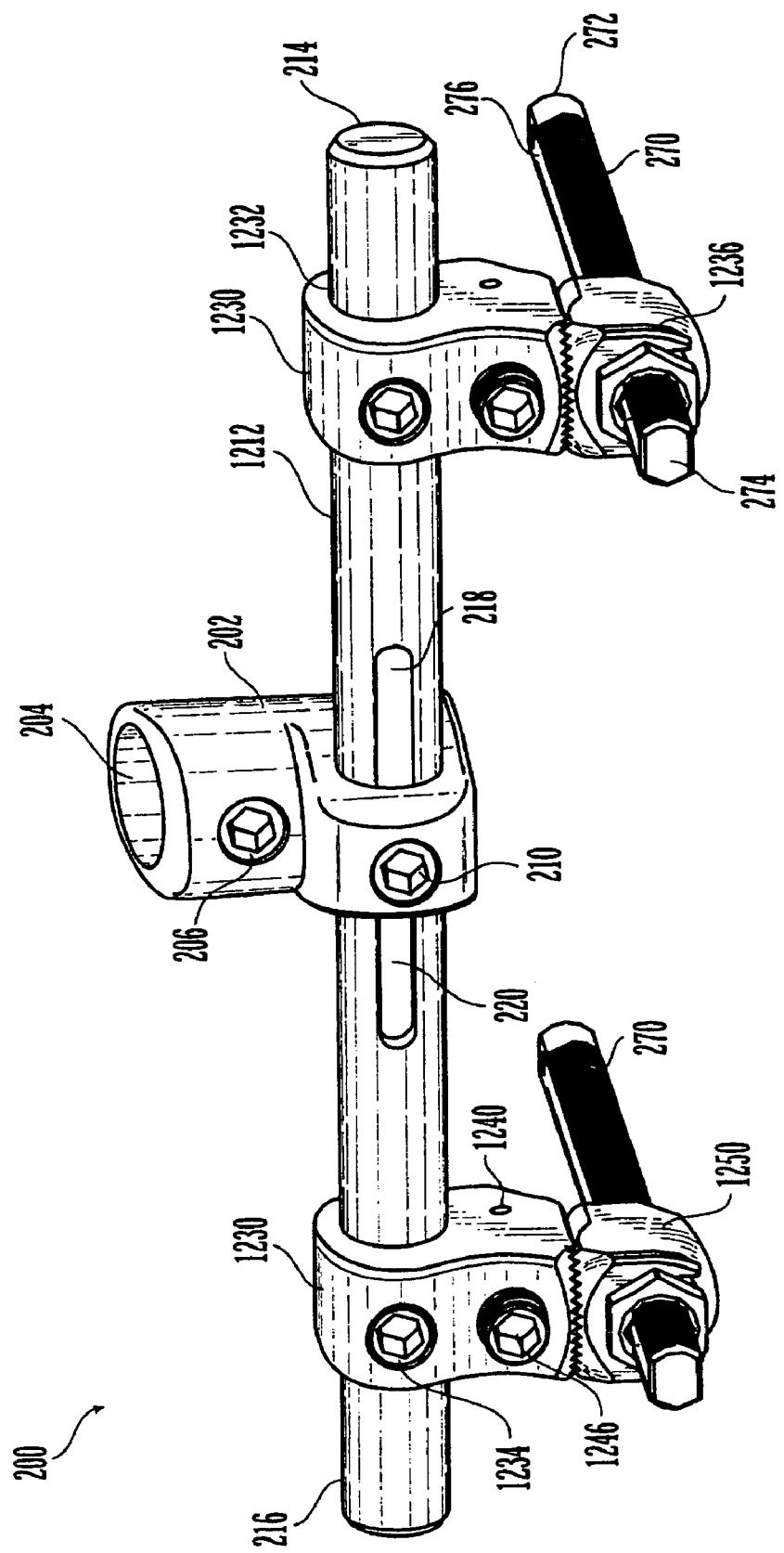
FIG. 12 is a perspective view of an alternate embodiment of the horizontal cross-piece assembly.
Figure 13A:
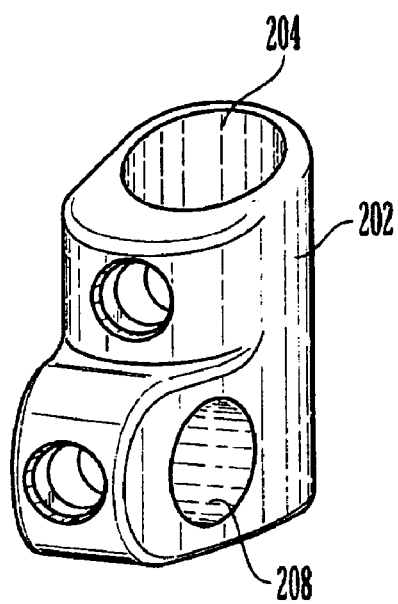
FIG. 13a is a perspective view of the central clamp of the horizontal cross-piece assembly.
Figure 13B:
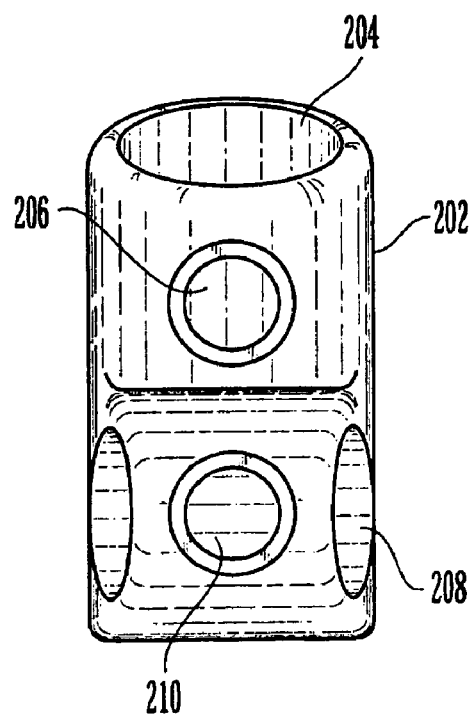
FIG. 13b is a front view of the central clamp of the horizontal cross-piece assembly.

As best shown in FIGS. 11 and 12, the horizontal cross-piece assembly 200 includes a central clamp 202, a horizontal rod 212, and two distractor clamps 230. The central clamp 202 connects the vertical central rod 150 to the horizontal rod 212. As shown in FIGS. 13a and 13b, the central clamp 202 may be a block member having two non-intersecting bores—vertical bore 204 and horizontal bore 208—extending therethrough. The vertical bore 204 extends through the central clamp 202 generally along the superior-inferior axis, while the horizontal bore 208 passes through the central clamp 202 generally along the medial-lateral axis. As previously stated, the central clamp 202 includes a set screw 206 for engaging the slot formed in the vertical central rod 150 thereby preventing rotation between the vertical rod 150 and the central clamp 202. Once tightened, the set screw 206 prevents movement of the central clamp 202 with respect to the vertical central rod 150. The horizontal bore 208 may be circular for mating with a cylindrical horizontal rod 212, thereby permitting rotation of the horizontal rod 212 relative to the central clamp 202. The central clamp 202 may also include a set screw 210 for engaging the horizontal rod 212. Once tightened, the set screw 210 prevents movement of the central clamp 202 with respect to the horizontal rod 212.

The horizontal rod 212 is generally oriented along an axis perpendicular to the longitudinal axis of the vertical central rod 150. The horizontal rod 212 interconnects the central clamp 202 and the distractor clamps 230, which, as shown, may be located one on each side of the central clamp 202. However, any number and configuration of distractor clamps 230 may be used. The horizontal rod 212 has a first end 214, a second end 216 and a central portion 218 disposed therebetween. The first and second ends 214, 216 each may slidably engage a bore 232 within a respective distractor clamp 230, while the central portion 218 of the horizontal rod 212 may slidably engage the horizontal bore 208 of the central clamp 202. The central portion 218 of the horizontal rod 212 may have a groove 220 along at least a portion of its length for accepting and engaging the horizontal set screw 210 of the central clamp 202. The groove 220 may interact with the set screw 210 to keep the horizontal rod 212 from rotating with respect to the central clamp 202.

As shown, the distractor clamps 230 may comprise a block member having a horizontal bore 232 for receiving the horizontal rod 212 and a distraction screw bore 236 for receiving a distraction screw 270. The horizontal bore 232 may be circular to mate with the circular cross-section of the horizontal rod 212. This configuration permits the distractor clamps 230 to be located virtually anywhere along the length of the horizontal rod 212, thus permitting the surgeon to adjust the lateral placement of the distraction screws 270 and footplates 300 attached thereto. Furthermore, the circular horizontal bore 232 permits the surgeon to rotate the distractor clamps 230 and the distraction screws 270 about the axis of the horizontal rod 212, thus permitting the surgeon to vary the angle of the distraction screws 270 with respect to the horizontal rod 212, and thereby providing an additional control over the angle and direction of distraction, particularly in the superior-inferior direction. Each distractor clamp 230 may also include a set screw 234, which when tightened prevents movement and rotation of the distractor clamp 230 with respect to the horizontal rod 212.

The distraction screw bore 236 generally has an axis orientated perpendicular to the axis of the horizontal rod 212. The distraction screw bore 236 may be configured to receive the distraction screw 270 and a distraction nut 238, e.g., a hex nut, etc., for threadedly engaging the distraction screw 270. Thus, rotation of the distraction nut 238 may draw the distraction screw 270 through the screw bore 236 to cause the distraction of an attached bone segment (to be described in more detail later).

With reference to FIGS. 12, 14a, 14b, 15a-15c, 16a, and 16b, each distractor clamp 1230 may also include a swivel feature. The swivel distractor clamp 1230 may be constructed from multiple pieces, each capable of swiveling with respect to its associated piece. As shown, the swivel distractor clamp 1230 may include a top piece 1240 and a bottom piece 1250, the top piece 1240 being associated with the horizontal rod 1212 and the bottom piece 1250 being associated with the distraction screw 270. That is, as best shown in FIGS. 14a, 14b, 15a-15c, 16a, and 16b, the top piece 1240 of the swivel distractor clamp 1230 may have the horizontal bore 1232 for slidably engaging the horizontal rod 1212, while the bottom piece 1250 may have the distraction screw bore 1236 for engaging the distraction screws 270. The top and bottom pieces 1240, 1250 may be connected by any appropriate manner know in the art to permit the bottom piece 1250, and thus the distraction screw 270 attached thereto, to rotate, with respect to the top piece 1240 and the associated horizontal rod 212. The bottom piece 1250 may swivel about an axis generally parallel to and offset from the axis of the vertical central rod 150. However, the axis of swivel is a matter of design choice and other swivel axes may be provided. Using a swivel distractor clamp 1230 provides a surgeon with yet another adjustment option in fixing the location of the distraction screws 270, and in turn, over the ultimate direction of distraction. Preferably, the swivel clamps 1230 may permit +/−20 degrees of rotation.

The top piece 1240 may include a vertical bore 1244 extending from the bottom surface 1242 of the top piece 1240 for receiving a vertical post 1254 extending from the top surface 1252 of the lower piece 1250, the vertical post 1254 and the vertical bore 1244 having mating cross-sections, thus permitting the bottom piece 1250 to rotate or swivel with respect to the top piece 1240, and thereby allowing for the transverse rotation of the distraction screws 270. The top piece 1240 may also contain a set screw 1246 having a tip for mating with a groove 1256 in the vertical post 1254, which when tightened prevents further rotation or swiveling between the top piece 1240 and the bottom piece 1250, thereby preventing the distraction screws 270 from further rotation. The bottom surface 1242 of the top piece 1240 and the top surface 1252 of the bottom piece 1250 may also contain interlocking teeth 1258 to provisionally lock, i.e., secure, the bottom portion 1250 with respect to the top portion 1240.

Figure 14A:
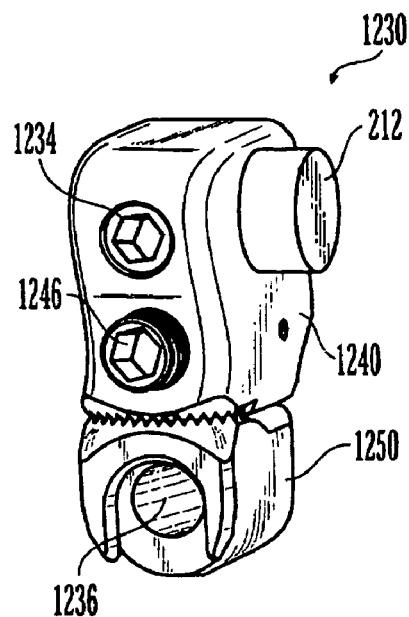
FIG. 14a is a perspective view of the swivel-type distractor clamp of the horizontal cross-piece assembly depicted in FIG. 12.
Figure 14B:
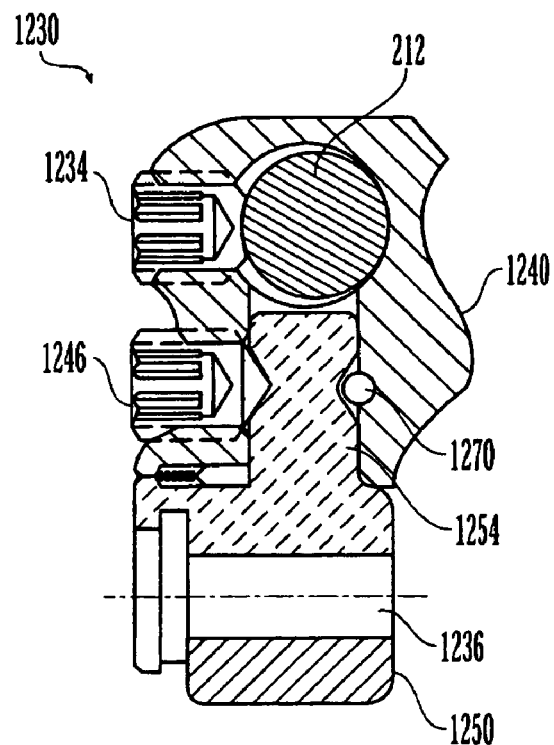
Figure 16A:
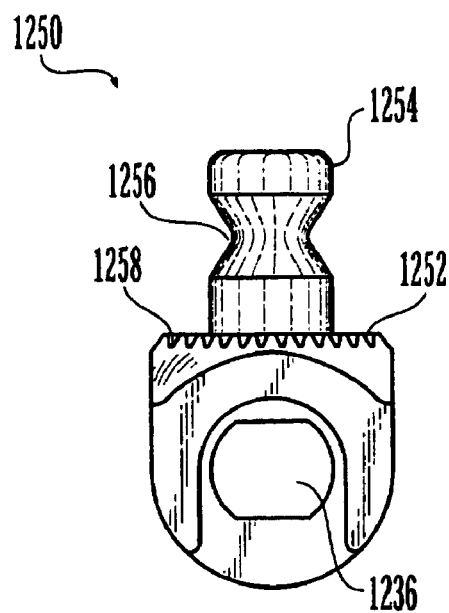
FIG. 16a is a front view of the bottom portion of the distractor clamp depicted in FIG. 12.
Figure 16B:
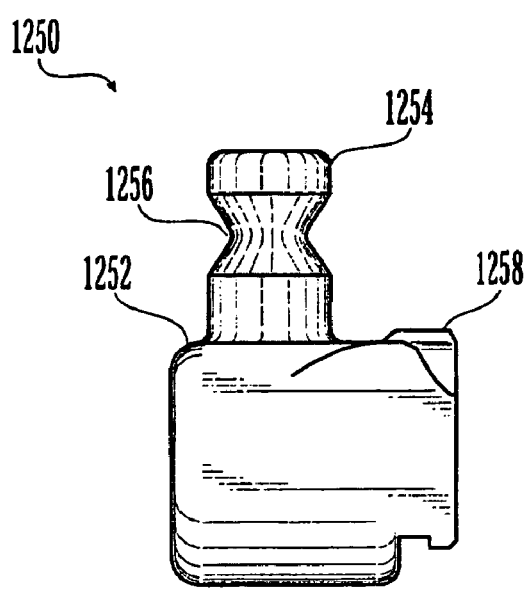

Furthermore, preferably, the top piece 1240 and the groove 1256 formed in the vertical post 1254 may be sized and configured to receive a pin 1270, as best shown in FIG. 14b. The pin 1270 is sized and configured to mate with the vertical post 1254 and the vertical bore 1244 formed in the top piece 1240 in order to prevent the top and bottom pieces 1240, 1250 of the distractor clamp 1230 from separating when the set screw 1246 is loosened.

Alternatively, the top and bottom pieces 1240, 1250 of the swivel clamp 1230 may be reversed. That is, the top piece 1240 of the swivel clamp 1230 may contain the distraction screw bore 1236 for engaging the distraction screw 270, while the bottom piece 1250 may have the horizontal bore 1232 for slidably engaging the horizontal rod 1212.

The distraction screws 270 may generally be oriented perpendicular to both the vertical central rod 150 and the horizontal rod 212, however, the swivel-type distractor clamp 1230 may allow adjustment of this orientation relative to the axis of the horizontal rod 1212. The distraction screws 270 may include a distal end 272 that points inward toward the patient's face, and a proximal end 274 which engages the distractor clamp 230, as discussed above. Preferably, the distraction screw 270 includes etched calibrations, i.e., markings, extending from the distal end 272 to the proximal end thereof to help the surgeon determine the exact amount of distraction performed. The distal end 272 of each distraction screw 270 may include a hole 276 drilled or otherwise formed therethrough. The hole 276 is generally configured to accept a wire 285, which may be used to interconnect the distraction screw 270 with a corresponding footplate assembly 300. Using a wire 285 to interconnect the distraction screws 270 with the bone-engaging portions 302 (to be discussed in more detail later) permits the midface distractor 10 to be easily disconnected and may eliminate the need for a second incision to remove the bone-engaging portions 302. That is, the bone-engaging portions 302 may be constructed with a low profile so that, if desired, they may be left attached to the patient's maxilla and zygoma with little, if any, visible indication thus eliminating the need for a second incision to remove the bone-engaging portions 302. Moreover, the bone-engaging portions 302 may be manufactured from a bioresorbable material, which may be left in the patient after the procedure. The bioresorbable footplates may naturally deteriorate over time, thus eliminating the need for their removal. Using a wire 285 permits the bone-engaging portions 302 to be easily disconnected from the distraction screws 270, thereby permitting the midface distractor 10 to be easily disconnected and removed from the patient's cranium. The wire 285 may be manufactured from any appropriate material known in the art including, but not limited to, 24 or 26 gauge stainless steel wire. Using a wire 285 however is not critical and alternatively, the distraction screws 270 may directly engage the bone-engaging portions 302.

Footplate Assemblies

The footplate assemblies 300 connect the distraction screws 270 to the targeted bone segments to be distracted. As shown in FIG. 1, the midface distractor 10 may have four footplate assemblies 300. However, as previously stated this number is not critical and any number of footplate assemblies 300 may be used. The midface distractor 10 may incorporate maxillary and zygomatic footplate assemblies that connect the targeted bone segments with respective distraction screws 270. The maxillary and zygomatic footplate assemblies may generally be configured to make the midface distractor 10 easier to attach and remove from the targeted bone segments, and to maximize patient comfort.

The maxillary footplate assembly 310 generally connects a maxillary bone segment, generally just above the tooth buds, to the horizontal cross-piece assembly 200. When more than one cross-piece assembly 200 is utilized, the maxillary footplate assembly 310 generally connects to the lower horizontal cross piece assembly 200. The zygomatic footplate assembly 340 connects a zygomatic bone segment to the upper cross-piece assembly 200 (when more than one horizontal cross-piece assembly is used).

The footplate assemblies 300 generally include a bone engaging portion 302 for directly engaging the maxilla or zygoma. The bone engaging portion 302 may be a footplate, and may be provided in a wide variety of shapes suitable for connection to the zygoma, maxilla, nose, infraorbital rim, or pyriform aperature as desired by the surgeon and as the particular bones permit and/or procedure requires. The bone engaging portions 302 may have one or more holes 304 therethrough for receiving bone engaging screws (not shown) for securing the portion to bone, the number of holes 304 being a matter of design choice. The bone-engaging portions 302 may be manufactured from any appropriate material known in the art, including but not limited to titanium, bioresorbable material, etc. Alternatively, the bone-engaging portion 302 of the maxillary footplate assembly 310 may be a rigid intra-oral splint, the oral splint permitting engagement of the midface distractor 10 with the patient's teeth, thus eliminating the need for installing bone screws into the maxilla. Any intra-oral splint known in the art may be used. In one embodiment, the intra-oral splint may include orthodontic bands fit to the primary or secondary molars, depending upon the patient's age. The orthodontic bands may be bent into close contact with most, if not all, of the teeth associated with the maxilla. The intra-oral splint may further include connecting wires, which protrude from the orthodontic bands. The connecting wires facilitate connection to the distraction screws 270 either directly or via a wire 285. The orthodontic band and connection wire may be manufactured by any appropriate material known in the art including, but not limited to, stainless steel wire, for example, 0.045 or 0.050 stainless steel wire.

Figure 17:
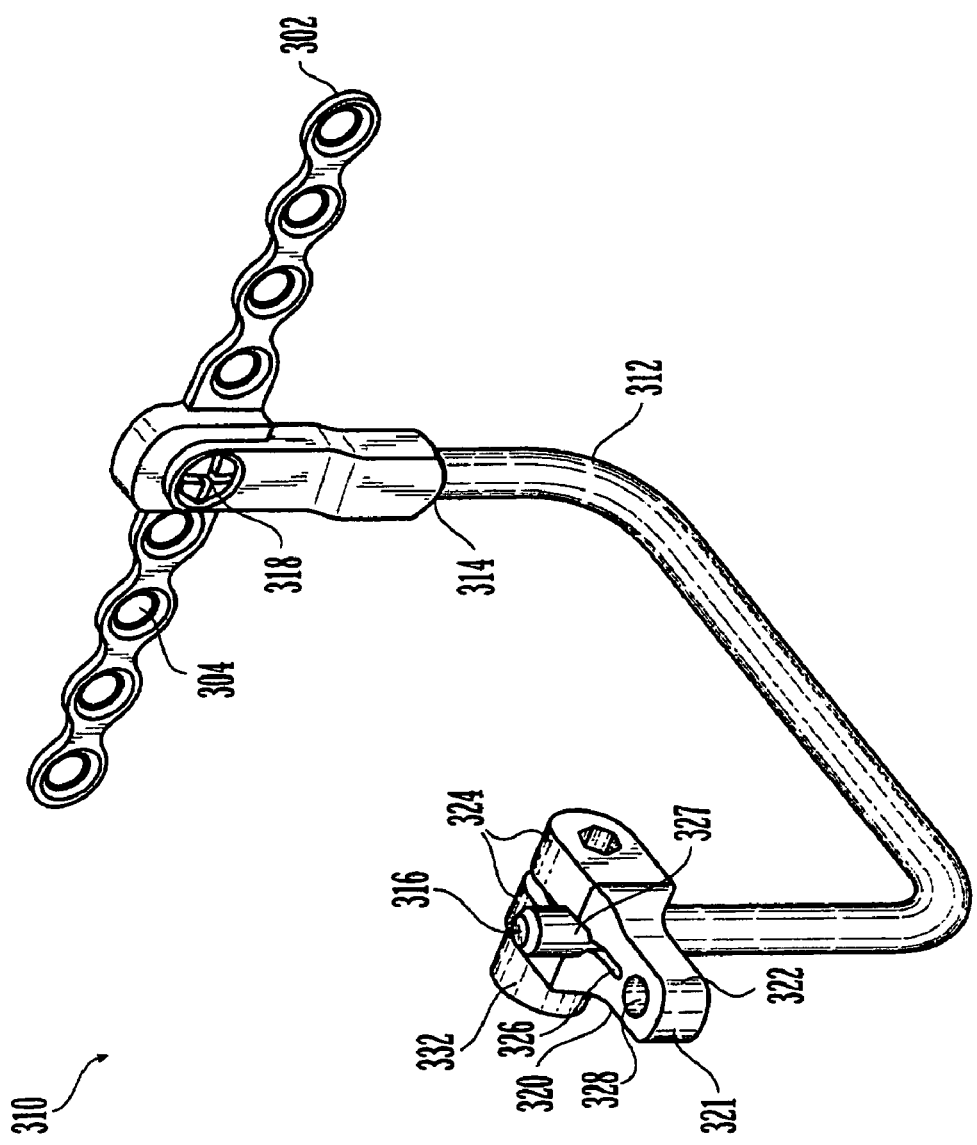
FIG. 17 is a perspective view of the maxillary footplate assembly depicted in FIG. 1.

As shown in FIG. 17, the maxillary footplate assembly 310 may also include a distractor-engaging portion 320, a distractor rod 312, and a bone engaging portion 302 (as described above). The distractor rod 312 is generally used to connect the bone-engaging portion 302 to the distractor-engaging portion 320, and has a first end 314 and a second end 316. The first end 314 of the distractor rod 312 connects to the bone engaging portion 302. This connection may be made by any method known in the art, including but not limited to: welding, screwing, bolting, machine screw, a slip-foot type connection, etc. In the illustrated embodiment, the distractor rod 312 and bone engaging portion 302 may be connected by a screw 318. The screw 318 permits the distractor rod 312 to be connected and disconnected from the bone-engaging portion 302 as necessary without requiring removal of the bone-engaging portion 302 from the patient. The second end 316 of the distractor rod 312 engages the distractor-engaging portion 320.

The distractor rod 312 may be manufactured from any material known in the art including, but not limited to, a strong, yet easily bendable material so that surgeons can shape the distractor rod 312 into any shape necessary to minimize interference with the patient's facial features. The material should still, however, be strong enough to resist deformation due to the forces exerted on it during the distraction process. As shown, the distractor rod 312 may be bent into a U-shape, so that when the maxillary footplate assembly engages the maxilla, the distractor-engaging portion 320 may be located outside the patient's mouth, while avoiding interference with the patient's lips.

The distractor-engaging portion 320 connects the bone-engaging portion 302 to the distraction screws 270. This connection may be by any appropriate method known in the art. Preferably, the distractor-engaging portion 320 may be a clamp 321 that slidably engages the distractor rod 312 so that the distractor-engaging portion 320 can be located anywhere along the length of the distractor rod 312. As shown, the clamp 321 may be a single-piece clamp including a base portion 322 with two arms 324 extending therefrom. The base portion 322 may include a vertical slot 326 extending along a portion of its length, the vertical slot 326 being provided with an internal widened jaw area 327 configured to engage the distractor rod 312. The vertical slot 326 permits the arms 324 of the clamp 321 to engage the distractor rod 312. The arms 324 also may include corresponding bores (not shown) for receiving a set screw 332, the tightening of which draws the arms 324 together, thereby clamping the distractor rod 312 therebetween, and preventing further movement of the clamp 321 with respect to the distractor rod 312. Furthermore, the base portion 322 of the clamp 321 may include a hole 328 therethrough for engaging the wire 285, which is then connected to the distraction screws 270, as best shown in FIG. 1, and as previously described.

Figure 18:
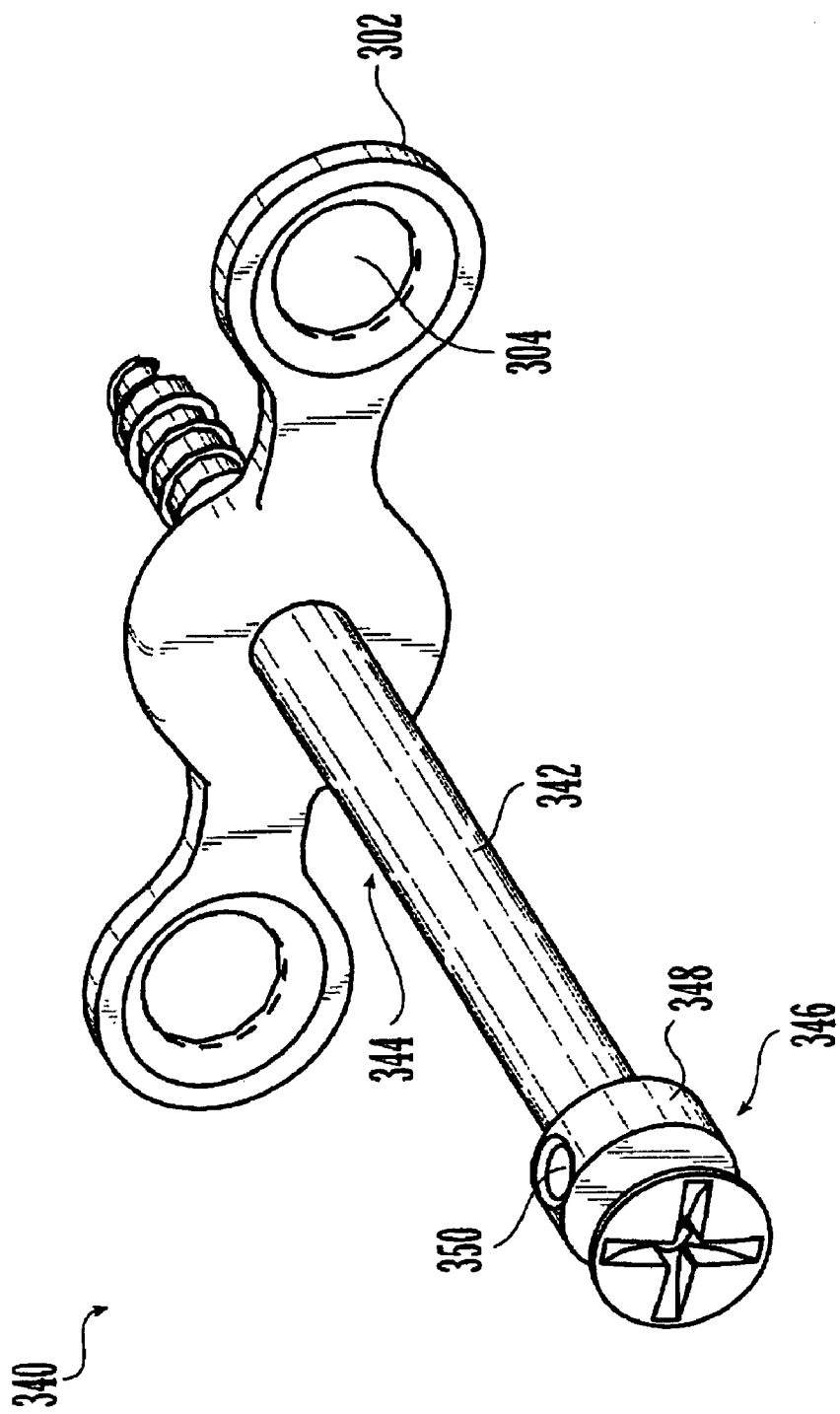
FIG. 18 is a perspective view of the zygomatic footplate assembly depicted in FIG. 1.

Similar to the maxillary footplate assemblies 310, the zygomatic footplate assembly 340 includes a bone engaging portion 302, as described above, for engaging a patient's zygoma. However, unlike the maxillary footplate assemblies 310 that include a distractor-engaging portion 320 and a distractor rod 312, the zygomatic footplate assemblies 340, as shown in FIG. 18, each may include a wire attachment screw 342 having a first end 344 and a second end 346. The first end 344 of the wire attachment screw 342 is sized and configured to threadedly engage and extend through a bore in the bone engaging portion 302 of the footplate assembly 300 so that the first end 344 of the screw 342 may also threadedly engage the patient's zygomatic bone. This permits the wire attachment screw 342 to engage the patient's bone at acute angles. The second end 346 of the screw 344 may include an enlarged head 348 with a hole 350 drilled therethrough for engaging a distraction screw 270 via a wire 285. The second end 346 may also include a tool-engaging mechanism on the end thereof for engaging a screwdriver, ratchet, etc., to facilitate installation and removal of the wire attachment screw 342 with respect to the bone engaging portion 302.

It should be noted that the maxillary 310 and zygomatic 340 footplate assemblies and their arrangements as described herein are preferred embodiments only and surgeons may if they so desire use only maxillary footplate assemblies 310, or only zygoma footplate assemblies 340. Furthermore, surgeons may attach the zygoma footplate assemblies 340 to the patient's maxilla, and attach the maxillary footplate assemblies 310 to the patient's zygoma. Finally, the distraction screws 270 may connect to the bone-engaging portions 302 directly or via a wire 285.

Installation and Removal Procedures and the
External Midface Distractor in Use

Installation of the midface distractor 10 may begin with the surgeon making the appropriate incisions to permit installation of the bone-engaging portions 302 to the targeted bone segment or bone segments. The surgeon then maps out the appropriate osteotomy, which may be a Lefort I, II, III or Monobloc configuration. The bone-engaging portions 302 may then be installed either intra-orally (when connecting to the patient's maxillary bones) or internally (when connecting to the patient's zygomatic bones). The appropriate bone cuts may then be made and the incisions may be closed.

The surgeon may then fit the halo assembly 20 to the patient's head by adjusting the lateral and longitudinal adjustment mechanisms of the halo assembly 20 and then engaging the halo 20 with the patient's head using skull fixation pins placed through the bores 71 in the side members 50. Alternatively, the surgeon may use the positional pins to temporarily position the location of the halo assembly 20 with respect to the patient's scalp until the central adjustment assembly 100, horizontal cross-piece assemblies 200, and distraction screws 270 are appropriately positioned.

The surgeon then selects the number of horizontal cross-piece assemblies 200 required, which is typically based upon the type of osteotomy being performed, for example, Lefort II, III and Monobloc generally require two horizontal cross-piece assemblies, while Lefort I generally only requires one. The horizontal cross-piece assemblies 200 may then be attached to the vertical central rod 150, which is attached to the central adjustment assembly 100, which may have already been connected to the halo assembly 20. The vertical central rod 150 is then adjusted and aligned using, inter alia, the lateral adjustment 33 and the central adjustment mechanism 100 to avoid interference with the patient's sight.

The surgeon then sets the angle of the distraction screws 270 based upon his/her determination as to the appropriate vector of distraction. The angle of the distraction screws 270 may be set by adjusting the location and angle of: the vertical central rod 150, the central adjustment assembly 100, the horizontal cross-piece assemblies 200 including the horizontal rod 212 and distractor clamps 230. Next, the surgeon attaches the wire 285, if used, to the distraction screws 270 and footplate assemblies 300. Thereafter, the set screws for each piece may be tightened, thus fixing the midface distractor 10 in place. Lastly, the surgeon tightens the wire 285 and confirms the advancement of the desired bone segments.

Note that while the preferred installation steps may be as described above, the steps of installation may vary, for example, the surgeon may map out the appropriate osteotomy prior to making any incision, or the surgeon may elect to install the bone-engaging portions 302 after making the appropriate osteotomy. Furthermore, the halo assembly 20 may be installed first, or after the osteotomy is performed.

Any number of variations to the installation procedure may be performed and yet still be within the scope of the present invention.

Once properly installed, the bone segments may be subjected to gradual incremental distraction by rotation of the distraction nut 238, which in turn distracts the engaged bone segments. The distraction screws 270 may be periodically (e.g. daily) rotated to incrementally distract the bone segment (usually by about 1 mm), until the desired distraction is achieved. The ultimate rate, rhythm, amount, and direction of distraction is left to the determination of the surgeon.

Furthermore, the present invention permits surgeons to alter the distraction vector of the distraction screws 270 during the distracting procedure, that is, after distraction has commenced. This is accomplished by either changing the position and/or angle of the distraction screws 270 by loosening the appropriate set screws and adjusting the position and/or angle of the vertical central rod 150, central adjustment assembly 100, or horizontal cross-piece assemblies 200 including the horizontal rod 212 and distractor clamps 230. Once properly repositioned, if necessary, the surgeon may then retighten the wires 285 and fix the new position of the midface distractor 10 by retightening the set screws.

To remove the midface distractor 10, the surgeon may cut the wires 285, if used, thus disconnecting the midface distractor 10 from the bone-engaging portions 302. Thereafter, the skull fixation pins (not shown) may be loosened and the entire assembly removed from the patient's head. The surgeon then removes the bone engaging portions 302, if necessary. Alternatively, as previously stated, the bone-engaging portions 302 may be designed with a low profile so that, if desired, they may be left attached to the patient's maxilla and zygoma with little, if any, visible indication thus eliminating the need for a second incision to remove the bone-engaging portions 302. Moreover, the bone-engaging portions 302 may be manufactured from a bioresorbable material, which may be left in the patient after the procedure. The bioresorbable footplates naturally deteriorating over time.

Finally, it should be noted that the midface distractor 10 of the present invention may be provided as a kit having various components, permitting the surgeon to select from a variety of pieces to customize the midface distractor 10 to the needs of each individual patient. For example, a kit may include several horizontal cross-piece assemblies 200, thus permitting surgeons to choose the number of cross-piece assemblies 200 to be installed. Additionally, the kit may contain varying sized distraction screws 270 having varying pitches, the varying pitches changing the amount of distraction per unit turn of the distraction screws 270 based upon the individual patient's needs. Furthermore, the kit may contain various sizes, shapes, materials of footplates 300, different sized horizontal 212 and vertical 150 rods, swivel and non-swivel distractor clamps 230, adjustable and non-adjustable center adjustment assemblies 100, etc.

The present invention has been described in connection with the preferred embodiments. These embodiments, however, are merely for example and the invention is not restricted thereto. It will be understood by those skilled in the art that other variations and modifications can easily be made within the scope of the invention as defined by the appended claims, thus it is only intended that the present invention be limited by the following claims.

What is claimed:

1. A distractor comprising
a halo assembly configured to attach to a patients head;
a vertical central rod having a longitudinal axis;

a central adjustment assembly comprising a rear portion and a front portion, wherein the rear portion is attached to the halo assembly and the front portion is attached to the vertical central rod;

at least one horizontal cross piece assembly attached to the vertical central rod, the at least one horizontal crosspiece assembly including at least one distraction element and at least one bone engaging portion; and wherein the front portion of the central adjustment assembly is angularly adjusted with respect to the rear portion in at least two degrees of freedom, the first degree of freedom being that the front portion is angularly adjusted by rotation in a medial-lateral direction with respect to the rear portion, and the second degree of freedom being that the front portion is angularly adjusted by rotation in a superior-inferior direction with respect to the rear portion.

2. The distractor according to claim 1, wherein the central adjustment assembly includes two angular adjustment mechanisms, one for providing angular adjustment of the front portion with respect to the rear portion about an axis extending perpendicular to the longitudinal axis of the vertical central rod, and the other for providing angular adjustment of the front portion with respect to the rear portion about an axis parallel to the longitudinal axis of the vertical central rod.

3. The distractor according to claim 2, wherein each of two angular adjustment mechanisms comprises at least one worm-gear mechanism.

4. The distractor according to claim 1, wherein the halo assembly further comprises a U-shaped member, the U-shaped member including a pair of mounting plates, two side members, and a central connecting hub; wherein each side member has a first end and a second end, the first end is attached to one of the mounting plates and the second end is attached to the central connecting hub.

5. The distractor according to claim 4, wherein the mounting plates are adjustably connected to the first end of the side member.

6. The distractor according to claim 5, wherein the mounting plates further comprises a top surface having a groove, and the first end of the side member has a dovetail for slidably engaging the groove.

7. The distractor according to claim 6, wherein the mounting plates further comprise a housing having a bore for receiving an adjustment screw, and the first end of the side member further includes an internally threaded bore for engaging the adjustment screw; rotation of the adjustment screw causing the side member and mounting plate to be axially displaceable with respect to one another.

8. The distractor according to claim 4, wherein the mounting plates further comprise a plurality of cranial fixation bores.

9. The distractor according to claim 8, wherein at least one of the plurality of bores is threaded for receiving an externally threaded skull fixation pin.

10. The distractor according to claim 9, wherein at least a portion of the externally threaded skull fixation pins includes a bone thread.

11. The distractor according to claim 10, wherein the plurality of bores include a first set of bores which have axes perpendicular to the plane of the mounting plate, and a second set of bores having axes substantially non-perpendicular to the plane of the mounting plate.

12. The distractor according to claim 4, wherein the connecting hub further comprises a central body and a frame adjustment screw, rotation of the frame adjustment screw causing a width of the halo assembly to be adjusted.

13. The distractor according to claim 12, wherein the connection hub is sized and configured to simultaneously engage two central adjustment assemblies.

14. The distractor according to claim 12, wherein the frame adjustment screw is a double threaded screw that mates with corresponding internally threaded bores formed in the second ends of the side members.

15. The distractor according to claim 12, wherein the connecting hub further comprises two rods located parallel to, and on either side of, the frame adjustment screw.

16. The distractor according to claim 4, wherein the connecting hub further comprises a top surface having a projection and the central adjustment assembly further comprises a bottom surface having a slot, the projection being slidably received within the slot.

17. The distractor according to claim 16, wherein the slot is a groove and the projection is a dovetail.

18. The distractor according to claim 4, wherein the rear portion mates with the connecting hub, and the front portion includes a bore for engaging the vertical central rod.

19. The distractor according to claim 18, wherein the vertical central rod has a slot for mating with a set screw in the bore for preventing rotation therebetween.

20. The distractor according to claim 1, wherein the distractor comprises two horizontal cross piece assemblies, one for connecting to at least one maxillary bone and the other for connection to at least one zygomatic bone.

21. The distractor according to claim 1, wherein the at least one horizontal cross-piece assembly further comprises a central clamp, a horizontal rod, two distractor clamps, and two distraction elements, the central clamp interconnecting the horizontal rod with the vertical central rod, and the distractor clamp interconnecting the horizontal rod with the distraction elements.

22. The distractor according to claim 21, wherein the distractor clamps are rotatably adjustable about the axis of the horizontal rod.

23. The distractor according to claim 21, wherein the distractor clamps further comprise a distracting element bore for receiving the distraction element.

24. The distractor according to claim 21, wherein the distractor clamp further comprises a top piece and a bottom piece, the top piece being angularly adjustable relative to the bottom piece.

25. The distractor according to claim 24, wherein the top piece and the bottom piece include a retention feature so that the top piece and the bottom piece can not be inadvertently separated with respect to one another.

26. The distractor according to claim 24, wherein the top piece and the bottom piece are angularly adjustable about an axis substantially parallel to the axis of the vertical central rod.

27. The distractor according to claim 21, wherein the distraction elements further comprise a distal end that points inward toward the patient's face and a proximal end associated with the distractor clamp.

28. The distractor according to claim 27, wherein the distal end of the distraction element further comprises a hole for receiving a wire, the wire being disposed between the distraction element and the bone engaging portion.

29. The distractor according to claim 1, wherein the bone engaging portion further comprises at least two footplate assemblies.

30. The distractor according to claim 29, wherein the at least two footplate assemblies are selected from the group consisting of at least two maxillary footplate assemblies and at least two zygomatic footplate assemblies.

31. The distractor according to claim 1, wherein the at least one footplate assembly further comprises a distractor-engaging portion for interconnecting the at least one footplate assembly and the distraction elements, and a distraction rod for interconnecting the bone-engaging portion and the distractor-engaging portion.

32. The distractor according to claim 31, wherein the distraction rod and bone engaging portion are releasably connected to one another.

33. The distractor according to claim 31, wherein the distractor engaging portion further comprises a single-piece clamp having a base portion with two arms extending therefrom, the base portion having a slot configured to engage the distraction rod and the arms having corresponding holes for engaging a wire, the wire interconnecting the distractor engaging portion and the distraction element.

34. The distractor according to claim 1, wherein the at least one footplate assembly further comprises a wire attachment screw, the wire attachment screw having a first end and a second end, wherein the first end threadedly engages and extends through a bore in the bone engaging portion so that the first end may also threadedly engage the patient's bone.

35. The distractor according to claim 34, wherein the second end has an enlarged head with a hole for engaging a respective distraction element via a wire.

36. A distractor comprising:
a halo assembly configured to attach to a patient's head;
a vertical central rod;
a central adjustment assembly comprising a rear portion attached to the halo assembly and a front portion attached to the vertical central rod, the front portion is angularly adjusted with respect to the rear portion in at least two degrees of freedom; and
at least one horizontal cross piece assembly attached to the vertical central rod, the at least one horizontal cross piece assembly including at least one distraction element and at least one bone engaging portion;
wherein the halo assembly further comprises at least one mounting plate and at least one side member, each side member having a first end and a second end, the first end is adjustably connected to the mounting plate;
wherein the halo assembly further comprises a U-shaped member, the U-shaped member including a pair of mounting plates having a top surface having a groove, two side members, and a central connecting hub; wherein each side member has a first end and a second end, the first end is attached to one of the mounting plates and having a dovetail which slidably engages the groove and the second end is adjustably connected to the central connecting hub.

37. The distractor according to claim 36, wherein the central adjustment assembly includes two angular adjustment mechanisms, one for providing angular adjustment of the front portion of the central adjustment assembly with respect to the rear portion about an axis extending perpendicular to the longitudinal axis of the vertical central rod, and the other for providing angular adjustment of the front portion with respect to the rear portion about an axis parallel to the longitudinal axis of the vertical central rod.

38. The distractor according to claim 37, wherein each of the two angular adjustment mechanisms comprises at least one worm-gear mechanism.

39. The distractor according to claim 36, wherein the mounting plates further comprises a housing having a bore for receiving an adjustment screw, and the first end of the side member further includes an internally threaded bore for engaging the adjustment screw; rotation of the adjustment screw causing the side member and mounting plate to be axially displaceable with respect to one another.

40. The distractor according to claim 36, wherein the mounting plates further comprise a plurality of cranial fixation bores.

41. The distractor according to claim 40, wherein at least one of the plurality of bores is threaded for receiving an externally threaded skull fixation pin.

42. The distractor according to claim 41, wherein at least a portion of the externally threaded skull fixation pins includes a bone thread.

43. The distractor according to claim 41, wherein the plurality of bores include a first set of bores which have axes perpendicular to the plane of the mounting plate, and a second set of bores having axes substantially non-perpendicular to the plane of the mounting plate.

44. The distractor according to claim 36, wherein the connecting hub further comprises a central body and a frame adjustment screw, rotation of the frame adjustment screw causing a width of the halo assembly to be adjusted.

45. The distractor according to claim 44, wherein the connection hub is sized and configured to simultaneously engage two central adjustment assemblies.

46. The distractor according to claim 44, wherein the frame adjustment screw is a double threaded screw that mates with corresponding internally threaded bores formed in the second ends of the side members.

47. The distractor according to claim 44, wherein the connecting hub further comprises two rods located parallel to, and on either side of, the frame adjustment screw.

48. The distractor according to claim 36, wherein the connecting hub further comprises a top surface having a projection and the central adjustment assembly further comprises a bottom surface having a slot, the projection being slidably received within the slot.

49. The distractor according to claim 48, wherein the slot is a groove and the projection is a dovetail.

50. The distractor according to claim 36, wherein the rear portion mates with the connecting hub, and the front portion includes a bore for engaging the vertical central rod.

51. The distractor according to claim 50, wherein the vertical central rod has a slot for mating with a set screw in the bore for preventing rotation therebetween.

52. The distractor according to claim 36, wherein the distractor comprises two horizontal cross piece assemblies, one for connecting to at least one maxillary bone and the other for connection to at least one zygomatic bone.

53. The distractor according to claim 36, wherein the at least one horizontal cross-piece assembly further comprises a central clamp, a horizontal rod, two distractor clamps, and two distraction elements, the central clamp interconnecting the horizontal rod with the vertical central rod, and the distractor clamp interconnecting the horizontal rod with the distraction elements.

54. The distractor according to claim 53, wherein the distractor clamps are rotatably adjustable about the axis of the horizontal rod.

55. The distractor according to claim 53, wherein the distractor clamps further comprise a distracting element bore for receiving the distraction element.

56. The distractor according to claim 53, wherein the distractor clamp further comprises a top piece and a bottom piece, the top piece being angularly adjustable relative to the bottom piece.

57. The distractor according to claim 56, wherein the top piece and the bottom piece include a retention feature so that the top piece and the bottom piece can not be inadvertently separated with respect to one another.

58. The distractor according to claim 56, wherein the top piece and the bottom piece are angularly adjustable about an axis substantially parallel to the axis of the vertical central rod.

59. The distractor according to claim 53, wherein the distraction elements further comprise a distal end that points inward toward the patient's face and a proximal end associated with the distractor clamp.

60. The distractor according to claim 59, wherein the distal end of the distraction element further comprises a hole for receiving a wire, the wire being disposed between the distraction element and the bone engaging portion.

61. The distractor according to claim 36, wherein the bone engaging portion further comprises at least one footplate assembly.

62. The distractor according to claim 61, wherein the at least one footplate assembly is selected from the group consisting of at least one maxillary footplate assembly and at least one zygomatic footplate assembly.

63. The distractor according to claim 61, wherein the at least one footplate assembly further comprises a distractor-engaging portion for interconnecting the at least one footplate assembly and the distraction elements, and a distraction rod for interconnecting the bone-engaging portion and the distractor-engaging portion.

64. The distractor according to claim 63, wherein the distraction rod and bone engaging portion are releasably connected to one another.

65. The distractor according to claim 63, wherein the distractor engaging portion further comprises a single-piece clamp having a base portion with two arms extending therefrom, the base portion having a slot configured to engage the distraction rod and the arms having corresponding holes for engaging a wire, the wire interconnecting the distractor engaging portion and the distraction element.

66. The distractor according to claim 61, wherein the at least one footplate assembly further comprises a wire attachment screw, the wire attachment screw having a first end and a second end, wherein the first end threadedly engages and extends through a bore in the bone engaging portion so that the first end may also threadedly engage the patient's bone.

67. The distractor according to claim 66, wherein the second end has an enlarged head with a hole for engaging a respective distraction element via a wire.

68. A distractor comprising:
a halo assembly configured to attach to a patient's head;
a vertical central rod;
a central adjustment assembly comprising a rear portion and a front portion, wherein the rear portion is attached to the halo assembly and the front portion is attached to the vertical central rod, wherein the front portion of the central adjustment assembly is angularly adjusted with respect to the rear portion in at least two degrees of freedom, the first degree of freedom being that the front portion is angularly adjusted by rotation in a medial-lateral direction with respect to the rear portion, and the second degree of freedom being that the front portion is angularly adjusted by rotation in a superior-inferior direction with respect to the rear portion, wherein the central adjustment assembly connects the vertical central rod to the halo assembly;
at least one horizontal cross piece assembly attached to the vertical central rod, the at least one horizontal cross piece assembly including at least one distraction element and at least one bone engaging portion comprising at least one footplate assembly selected from the group consisting of at least one maxillary footplate assembly and at least one zygomatic footplate assembly;
wherein the at least one horizontal cross-piece assembly includes a central clamp, a horizontal rod, and at least one distractor clamp, the central clamp interconnects the horizontal rod with the vertical central rod, and the distractor clamp interconnects the horizontal rod with the distraction element;
wherein the distractor clamp includes a top piece attached to the horizontal cross-piece and a bottom piece including a bore that is engaged with distraction screw;
wherein the top piece and bottom piece are connected to each other so that the bottom piece and distraction screw are rotatable with respect to the top piece and horizontal rod.

69. The distractor according to claim 68, wherein the halo assembly further comprises a U-shaped member, the U-shaped member including a pair of mounting plates, two side members, and a central connecting hub; wherein each side member has a first end and a second end, the first end is attached to one of the mounting plates and the second end is attached to the central connecting hub.

70. The distractor according to claim 69, wherein the mounting plates are adjustably connected to the first end of the side member.

71. The distractor according to claim 70, wherein the mounting plates further comprises a top surface having a groove, and the first end of the side member has a dovetail for slidably engaging the groove.

72. The distractor according to claim 71, wherein the mounting plates further comprises a housing having a bore for receiving an adjustment screw, and the first end of the side member further includes an internally threaded bore for engaging the adjustment screw; rotation of the adjustment screw causing the side member and mounting plate to be axially displaceable with respect to one another.

73. The distractor according to claim 69, wherein the mounting plates further comprise a plurality of cranial fixation bores.

74. The distractor according to claim 73, wherein at least one of the plurality of bores is threaded for receiving an externally threaded skull fixation pin.

75. The distractor according to claim 74, wherein at least a portion of the externally threaded skull fixation pins includes a bone thread.

76. The distractor according to claim 74, wherein the plurality of bores include a first set of bores which have axes perpendicular to the plane of the mounting plate, and a second set of bores having axes substantially non-perpendicular to the plane of the mounting plate.

77. The distractor according to claim 69, wherein the connecting hub further comprises a central body and a frame adjustment screw, rotation of the frame adjustment screw causing the overall width of the halo assembly to be adjusted.

78. The distractor according to claim 77, wherein the connection hub is sized and configured to simultaneously engage two central adjustment assemblies.

79. The distractor according to claim 77, wherein the frame adjustment screw is a double threaded screw that mates with corresponding internally threaded bores formed in the second ends of the side members.

80. The distractor according to claim 77, wherein the connecting hub further comprises two rods located parallel to, and on either side of, the frame adjustment screw.

81. The distractor according to claim 69, wherein the connecting hub further comprises a top surface having a projection and the central adjustment assembly further comprises a bottom surface having a slot , the projection being slidably received within the slot.

82. The distractor according to claim 81, wherein the slot is a groove and the projection is a dovetail.

83. The distractor according to claim 69, wherein the central adjustment assembly further comprises a front portion and a rear portion, the rear portion mates with the connecting hub, and the front portion includes a bore for engaging the vertical central rod.

84. The distractor according to claim 83, wherein the vertical central rod has a slot for mating with a set screw in the bore for preventing rotation therebetween.

85. The distractor according to claim 68, wherein the distractor comprises two horizontal cross piece assemblies, one for connecting to at least one maxillary bone and the other for connection to at least one zygomatic bone.

86. The distractor according to claim 68, wherein the at least one horizontal cross-piece assembly farther comprises a central clamp, a horizontal rod, two distractor clamps, and two distraction elements, the central clamp interconnecting the horizontal rod with the vertical central rod, and the distractor clamp interconnecting the horizontal rod with the distraction elements.

87. The distractor according to claim 86, wherein the distractor clamps are rotatably adjustable about the axis of the horizontal rod.

88. The distractor according to claim 86, wherein the distractor clamps further comprise a distracting element bore for receiving the distraction element.

89. The distractor according to claim 86, wherein the distractor clamp further comprises a top piece and a bottom piece, the top piece being angularly adjustable relative to the bottom piece.

90. The distractor according to claim 89, wherein the top piece and the bottom piece include a retention feature so that the top piece and the bottom piece can not be inadvertently separated with respect to one another.

91. The distractor according to claim 89, wherein the top piece and the bottom piece are angularly adjustable about an axis substantially parallel to the axis of the vertical central rod.

92. The distractor according to claim 86, wherein the distraction elements further comprise a distal end that points inward toward the patient's face and a proximal end associated with the distractor clamp.

93. The distractor according to claim 92, wherein the distal end of the distraction element further comprises a hole for receiving a wire, the wire being disposed between the distraction element and the bone engaging portion.

94. The distractor according to claim 68, wherein the bone engaging portion further comprises at least two footplate assemblies.

95. The distractor according to claim 94, wherein the at least two footplate assemblies are selected from the group consisting of at least two maxillary footplate assemblies and at least two zygomatic footplate assemblies.

96. The distractor according to claim 68, wherein the at least one footplate assembly further comprises a distractor-engaging portion for interconnecting the at least one footplate assembly and the distraction elements, and a distraction rod for interconnecting the bone-engaging portion and the distractor-engaging portion.

97. The distractor according to claim 96, wherein the distraction rod and bone engaging portion are releasably connected to one another.

98. The distractor according to claim 96, wherein the distractor engaging portion further comprises a single-piece clamp having a base portion with two arms extending therefrom, the base portion having a slot configured to engage the distraction rod and the arms having corresponding holes for engaging a wire, the wire interconnecting the distractor engaging portion and the distraction element.

99. The distractor according to claim 68, wherein the at least one footplate assembly further comprises a wire attachment screw, the wire attachment screw having a first end and a second end, wherein the first end threadedly engages and extends through a bore in the bone engaging portion so that the first end may also threadedly engage the patient's bone.

100. The distractor according to claim 99, wherein the second end has an enlarged head with a hole for engaging a respective distraction element via a wire.

\* \* \* \* \*